US010514586B2

(12) United States Patent
Tzang et al.

(10) Patent No.: US 10,514,586 B2
(45) Date of Patent: Dec. 24, 2019

(54) METHODS AND SYSTEMS FOR CONTROL OF NONLINEAR LIGHT TRANSMISSION

(71) Applicant: The Regents of the University of Colorado, a body corporate, Denver, CO (US)

(72) Inventors: Omer Tzang, Boulder, CO (US); Rafael Piestun, Boulder, CO (US); Antonio Miguel Caravaca-Aguirre, Boulder, CO (US); Kelvin Wagner, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/039,156

(22) Filed: Jul. 18, 2018

(65) Prior Publication Data

US 2019/0025668 A1 Jan. 24, 2019

Related U.S. Application Data

(60) Provisional application No. 62/533,900, filed on Jul. 18, 2017.

(51) Int. Cl.
*G02F 1/365* (2006.01)
*G02F 1/35* (2006.01)

(52) U.S. Cl.
CPC ............ *G02F 1/365* (2013.01); *G02F 1/3501* (2013.01); *G02F 1/3536* (2013.01);
(Continued)

(58) Field of Classification Search
CPC ...... G02F 1/365; G02F 1/3501; G02F 1/3536; G02F 2203/26; G02F 2201/58; G02F 2201/05; G02F 2201/02
See application file for complete search history.

(56) References Cited

U.S. PATENT DOCUMENTS 8,730,573 B2 * 5/2014 Betzig ...................... G01J 9/00 250/461.2
2003/0076571 A1 4/2003 MacAulay et al.
(Continued)

OTHER PUBLICATIONS

Barsi, Christopher et al., "Imaging Through Nonlinear Media Using Digital Holography," Nature Photonics, vol. 3, pp. 211-215, Apr. 2009.
(Continued)

*Primary Examiner* — Ryan A Lepisto

(57) ABSTRACT

Recent remarkable progress in wave-front shaping has enabled control of light propagation inside linear media to focus and image through scattering objects. In particular, light propagation in multimode fibers comprises complex intermodal interactions and rich spatiotemporal dynamics. Control of physical phenomena in multimode fibers and its applications is in its infancy, opening opportunities to take advantage of complex mode interactions. Various embodiments of the present technology provide wave-front shaping for controlling nonlinear phenomena in multimode fibers. Using a spatial light modulator at the fiber's input and a genetic algorithm optimization, some embodiments control a highly nonlinear stimulated Raman scattering cascade and its interplay with four wave mixing via a flexible implicit control on the superposition of modes that are coupled into the fiber.

20 Claims, 20 Drawing Sheets

(52) U.S. Cl.
CPC ...... *G02F 2201/02* (2013.01); *G02F 2201/05* (2013.01); *G02F 2201/58* (2013.01); *G02F 2203/26* (2013.01)

(56) References Cited

U.S. PATENT DOCUMENTS

| | | | | |
|---|---|---|---|---|
| 2005/0078924 | A1 | 4/2005 | Viellerobe et al. | |
| 2014/0235948 | A1* | 8/2014 | Mahalati .................. | A61B 1/07 600/160 |
| 2017/0153440 | A1 | 6/2017 | Caravaca-Aguirre et al. | |
| 2017/0299900 | A1* | 10/2017 | Montoya ............... | G02F 1/0115 |

OTHER PUBLICATIONS

Bowers, Mark W. et al., "Brillouin-Enhanced Four-Wave-Mixing Vector Phase-Conjugate Mirror With Beam-Combining Capability," Optics Letters, vol. 22, No. 6, pp. 360-362, Mar. 15, 1997.
Caravaca-Aguirre, Antonio M. et al., "Real-Time Resilient Focusing Through A Bending Multimode Fiber," Optics Express, vol. 21, No. 10, pp. 12881-12887, May 20, 2013.
Caravaca-Aguirre, Antonio M. et al., "Single Multimode Fiber Endoscope," Optics Express, vol. 25, No. 3, pp. 1656-1665, Feb. 6, 2017.
Chiang, Kin S., "Stimulated Raman Scattering in A Multimode Optical Fiber: Self-Focusing or Mode Competition?," Optics Communications, vol. 95, pp. 235-238, Jan. 15, 1993.
Choi, Youngwoon et al., "Scanner-Free and Wide-Field Endoscopic Imaging by Using A Single Multimode Optical Fiber," Physical Review Letters, vol. 109, 203901-1-203901-5, Nov. 16, 2012.
Chraplyvy, Andrew R., "Limitations on Lightwave Communications Imposed by Optical-Fiber Nonlinearities," Journal of Lightwave Technology, vol. 8, No. 10, pp. 1548-1557, Oct. 1990.
Cizmar, Tomas et al., "Exploiting Multimode Waveguides for Pure Fibre-Based Imaging," Nature Communications, pp. 1-9, Aug. 28, 2012.
Cohen, Oren et al., "Observation of Random-Phase Lattice Solitons," Nature, vol. 433, pp. 500-503, Feb. 3, 2005.
Conkey, Donald B. et al., "Genetic Algorithm Optimization for Focusing Through Turbid Media in Noisy Environments," Optics Express, vol. 20, No. 5, pp. 4840-4849, Feb. 27, 2012.
Couny, F. et al., "Generation and Photonic Guidance of Multi-Octave Optical-Frequency Combs," Science, vol. 318, pp. 1118-1121, Nov. 16, 2007.
Demas, J. et al., "Intermodal Nonlinear Mixing With Bessel Beams in Optical Fiber," Optica, vol. 2, No. 1, pp. 14-17, Jan. 2015.
Dupiol, R. et al., "Far-Detuned Cascaded Intermodal Four-Wave Mixing in A Multimode Fiber," Optics Letters, vol. 42, No. 7, pp. 1293-1296, Apr. 1, 2017.
Essiambre, Rene-Jean et al., "Capacity Limits of Optical Fiber Networks," Journal of Lightwave Technology, vol. 28, No. 4, pp. 662-701, Feb. 15, 2010.
Florentin, Raphael et al., "Shaping the Light Amplified in A Multimode Fiber," Light: Science & Applications, vol. 6, 9 pages, Feb. 24, 2017.
Frostig, Hadas et al., "Focusing Light by Wavefront Shaping Through Disorder and Nonlinearity," Optica, vol. 4, No. 9, pp. 1073-1079, Sep. 7, 2017.
Gong, Mali et al., "Numerical Modeling of Transverse Mode Competition in Strongly Pumped Multimode Fiber Lasers and Amplifiers," Optics Express, vol. 15, No. 6, pp. 3236-3246, Mar. 19, 2007.
Katz, Ori et al., "Looking Around Corners and Through Thin Turbid Layers in Real Time With Scattered Incoherent Light," Nature Photonics, 5 pages, Jul. 15, 2012.
Katz, Ori et al., "Noninvasive Nonlinear Focusing and Imaging Through Strongly Scattering Turbid Layers," Optica, vol. 1, No. 3, pp. 170-174, Sep. 2014.
Krupa, Katarzyna, et al., "Observation of Geometric Parametric Instability Induced by The Periodic Spatial Self-Imaging of Multimode Waves," Physical Review Letters, vol. 116, pp. 183901-1-183901-5, May 6, 2016.
Krupa, K. et al., "Spatial Beam Self-Cleaning in Multimode Fiber," Cornell University, 6 pages, Mar. 9, 2016.
Li, Guifang et al., "Space-Division Multiplexing: The Next Frontier in Optical Communication," Advances in Optics and Photonics, vol. 6, pp. 413-487, Dec. 23, 2014.
Masihzadeh, Omid et al., "Enhanced Spatial Resolution in Third-Harmonic Microscopy Through Polarization Switching," Optics Letters, vol. 34, No. 8, pp. 1240-1242, Apr. 15, 2009.
Mosk, Allard P. et al., "Controlling Waves in Space and Time for Imaging and Focusing in Complex Media," Nature Photonics, vol. 6, pp. 283-292, May 2012.
Nazemosadat, Elham et al., "Phase Matching for Spontaneous Frequency Conversion Via Four-Wave Mixing in Graded-Index Multimode Optical Fibers," Journal of the Optical Society of America B, vol. 33, No. 2, pp. 144-150, Feb. 2016.
Papadopoulos, Ioannis N. et al., "High-Resolution, Lensless Endoscope Based on Digital Scanning Through A Multimode Optical Fiber," Biomedical Optics Express, vol. 4, No. 2, pp. 260-270, Feb. 1, 2013.
Park, Jung-Hoon et al., "High-Resolution In Vivo Imaging of Mouse Brain Through The Intact Skull," PNAS, vol. 112, No. 30, pp. 9236-9241, Jul. 28, 2015.
Polley, Arup et al., "Raman Amplification in Multimode Fiber," IEEE Photonics Technology Letters, vol. 19, No. 4, pp. 218-220, Feb. 15, 2007.
Popoff, S. M. et al., "Measuring The Transmission Matrix in Optics: An Approach to The Study and Control of Light Propagation in Disordered Media," Physical Review Letters, vol. 104, pp. 100601-1-100601-4, Mar. 12, 2010.
Pourbeyram, Hamed et al., "Photon Pair Generation in Multimode Optical Fibers Via Intermodal Phase Matching," Physical Review A, vol. 94, pp. 023815-1-023815-10, Aug. 5, 2016.
Pourbeyram, Hamed et al., "Stimulated Raman Scattering Cascade Spanning The Wavelength Range of 523 to 1750 nm Using A Graded-Index Multimode Optical Fiber," Applied Physics Letters, vol. 102, pp. 201107-1-201107-4, May 21, 2013.
Qiao, Yanqi et al., "Second-Harmonic Focusing by A Nonlinear Turbid Medium Via Feedback-Based Wavefront Shaping," Optics Letters, vol. 42, No. 10, pp. 1895-1898, May 15, 2017.
Richardson, D. J. et al., "High Power Fiber Lasers: Current Status and Future Perspectives," J. Opt. Soc. Am. B, vol. 27, No. 11, pp. B63-B92, Nov. 2010.
Rosman, G., "High-Order Comb Spectrum From Stimulated Raman Scattering in A Silica-Core Fibre," Optical and Quantum Electronics, vol. 14, pp. 92-93, 1982.
Sharma, A. et al., "Four-Photon-Mixing-Mediated Stimulated Raman Scattering in A Multimode Optical Fiber," Optics Letters, vol. 19, No. 15, pp. 1122-1124, Aug. 1, 1994.
Shibata, N. et al., "Refractive Index Dispersion of Lightguide Glasses At High Temperature," Electronics Letters, vol. 17, No. 8, pp. 310-311, Apr. 16, 1981.
Stolen, Rogers H., "Phase-Matched-Stimulated Four-Photon Mixing in Silica-Fiber Waveguides," IEEE Journal of Quantum Electronics, vol. QE-11, No. 3, pp. 100-103, Mar. 1975.
Stolen, R. H. et al., "Phase-Matched Three-Wave Mixing in Silica Fiber Optical Waveguides," Applied Physics Letters, vol. 24, No. 7, pp. 308-310, Apr. 1, 1974.
Stolen, R. H. et al., "Raman Oscillation in Glass Optical Waveguide," Appl. Phys. Lett., vol. 20, No. 2, pp. 62-64, Jan. 15, 1972.
Sun, Can et al., "Spectral Dynamics of Spatially Incoherent Modulation Instability," Physical Review Letters, vol. 108, pp. 263902-1-263902-5, Jun. 29, 2012.
Tzang, Omer et al., "Lock-In Detection of Photoacoustic Feedback Signal for Focusing Through Scattering Media Using Wave-Front Shaping," Optics Express, vol. 24, No. 24, pp. 28122-28130, Nov. 28, 2016.
Tzang, Omer et al., "Thermal Expansion Feedback for Wave-Front Shaping," Optics Express, vol. 25, No. 6, pp. 6122-6131, Mar. 20, 2017.

(56) References Cited

OTHER PUBLICATIONS

Vellekoop, I. M. et al., "Focusing Coherent Light Through Opaque Strongly Scattering Media," Optics Letters, vol. 32, No. 16, pp. 2309-2311, Aug. 15, 2007.
Wright, Logan G. et al., "Controllable Spatiotemporal Nonlinear Effects in Multimode Fibres," Nature Photonics, vol. 9, pp. 306-310, May 2015.
Wright, Logan G. et al., "Self-Organized Instability in Graded-Index Multimode Fibres," Nature Photonics, vol. 10, pp. 771-777, Dec. 2016.
Wright, Logan G. et al., "Spatiotemporal Dynamics of Multimode Optical Solitons," Optics Express, vol. 23, No. 3, pp. 3492-3506, Feb. 9, 2015.
Wright, Logan G. et al., "Ultrabroadband Dispersive Radiation by Spatiotemporal Oscillation of Multimode Waves," Physical Review Letters, vol. 115, pp. 223902-1-223902-5, Nov. 27, 2015.
Xu, Xiao et al., "Time-Reversed Ultrasonically Encoded Optical Focusing Into Scattering Media," Nature Photonics, vol. 5, pp. 154-157, Mar. 2011.
International Application No. PCT/US2018/042742, International Search Report & Written Opinion, 10 pages, dated Nov. 7, 2018.

* cited by examiner

METHODS AND SYSTEMS FOR CONTROL OF NONLINEAR LIGHT TRANSMISSION

CROSS-REFERENCE TO RELATED APPLICATIONS

This application claims priority to U.S. Provisional Application Ser. No. 62/533,900 filed Jul. 18, 2017 which is incorporated herein by reference in its entirety for all purposes.

STATEMENT REGARDING FEDERALLY SPONSORED RESEARCH

This invention was made with government support under grant number 1611513 and 1548924 awarded by the National Science Foundation. The government has certain rights in the invention.

TECHNICAL FIELD

Various embodiments of the present technology generally relate to wave-front shaping and control of light propagation in multimode fibers. More specifically, some embodiments of the present technology relate to wave-front shaping in nonlinear multimode fibers.

BACKGROUND

Wavefront shaping in random media is a high visibility topic with both fundamental implications and many exciting applications such as focusing and imaging through turbid media, looking behind corners and through fog, and using multimode fibers as miniature endoscopes. Another important field encompasses the dynamics of propagating modes in multimode fibers, involve intriguing physics and opportunities for application. In particular, nonlinearities in multimode fibers remains a largely unexplored field with opportunities to exploit the multimode degrees of freedom for controlling spatial-spectral-temporal interactions.

SUMMARY

Systems and methods are described for wave-front shaping to control nonlinear interactions in complex media. More specifically, some embodiments of the present technology relate to wave-front shaping in nonlinear multimode fibers. Various embodiments provide for a new kind of control that enables optimization of highly nonlinear interactions through fibers. Using wave-front shaping at the input, various embodiments can control the generation of nonlinear stimulated-Raman-scattering cascades and four-wave-mixing. Several novel phenomena and examples are described herein including the enhancement, suppression, and spectral shifting of the highly nonlinear multimode dynamics.

The techniques presented herein for nonlinear wave-front shaping open opportunities for characterization and control of rich spatiotemporal dynamics in multimode fibers. The adaptive optimization, used in some embodiments, represents an approach to solve the nonlinear inverse problem of finding a tailored superposition of modes at the input of the fiber. Potential applications include, but are not limited to, nonlinear frequency generation, high power MMF lasers, nonlinear endoscopy, and nonlinearity suppression in multimode fibers. The latter is important for optical fiber communications. Moreover, some embodiments allow for characterizing and controlling rich spatiotemporal dynamics in MMF.

Some embodiments include a system to control the spatial, spectral, polarization and/or temporal distribution of light. The system can include a light source, a spatial light modulator, a medium, a detection system and a control system. The light source can be configured to generate a light. The light source can a pulsed laser such as a nanosecond pulsed laser, a picosecond pulsed laser, or a femtosecond pulsed laser. The spatial light modulator (e.g., a liquid crystal spatial light modulator, a deformable mirror, a digital light projector, a segmented mirror, etc.) can have a variable mask to modify one or more properties of the light generated by the light source. The spatial light modulator includes independent macro pixels whose phase varies between zero and $2\pi$.

The medium (e.g., a waveguide, a multicore fiber, a multimode fiber, or other complex medium) can have a proximal end to receive a modified light from the spatial light modulator and guide the modified light to a distal end. The detection system can evaluate the one or more properties produced by the modified light at the distal end of the medium. The control system can be communicably coupled to the spatial light modulator and the detection system. The control system can be configured to evaluate the one or more properties produced by the modified light at the distal end of the medium. In some embodiments, the control system can generate an updated mask that enhances the one or more properties of the modified light at the distal end of the medium. The control system may also be configured to transmit a signal to the spatial light modulator to implement the updated mask. The detection system can include at least one among a spectrometer, a detector array, a camera, a photodetector, an autocorrelator, or a pulse characterization system.

In some embodiments the control system can generate the updated mask using an optimization algorithm, genetic algorithm, machine learning algorithm that optimizes an objective function. The control system may also be configured to control at least one of the following properties: the generation of nonlinear stimulated-Raman-scattering cascades and four-wave-mixing, the polarization of the output light, the pulse shape and duration of the output light, the spectrum of the output light, the spatial shape distribution of the output light, or the reduction of nonlinear effects.

Some embodiments provide a method for shaping multimode dynamics in a transmission medium. A property of a light can be measured at a distal end of a transmission medium. The controller can construct or select a phase mask (or changes thereof) to shape the property of the light as measured at the distal end of the transmission medium. The spatial light modulator can then be instructed to apply the phase mask to an input light generated by a light source to selectively tune nonlinear interactions within the transmission medium. The light can be filtered at the distal end of the transmission medium. The transmission medium can include a waveguide, a multimode fiber, a multicore fiber, a step index fiber, or a graded indexed (GRIN) fiber. Some embodiments can generate the light using a femtosecond pulsed laser, a picosecond pulsed laser, or a nanosecond pulsed laser.

The control system can be configured to control at least one of the following properties: the generation of nonlinear stimulated-Raman-scattering cascades and four-wave-mixing, the polarization of the output light, the pulse shape and/or duration of the output light, the spectrum of the output light, the spatial shape distribution of the output light, the reduction of nonlinear effects. The light is used to transmit information (e.g., as in a communication system). As such, some embodiments embed information into the light. The light source can include a laser light system.

Some embodiments provide an optical system with dynamic feedback control to enhance spatial, spectral, and/or temporal distributions of a light generated by a light source (e.g., a nanosecond pulsed laser, a picosecond pulsed laser, a femtosecond pulsed laser, or the like). The optical system can include a processor, a spatial light modular (e.g., a liquid crystal spatial light modulator, a deformable mirror, a digital light projector, or a segmented mirror, or the like), a medium, a detection system, and/or a control system. In accordance with various embodiments, the spatial light modulator can have an input to receive the light generated by the light source, a set of independent macro pixels that can be set by a variable mask to generate a modified light by changing one or more properties of the light generated by the light source, and an output to transmit the modified light outside of the spatial light modulator.

The medium (e.g., a waveguide, a multi-core fiber, a multimode fiber, etc.) can transmit the modified light entering a proximal end to a distal end. During the transmission of the light, the one or more aberrations or nonlinearities may be introduced into the modified light. The detection system can evaluate the one or more properties produced by the modified light at the distal end of the medium. The control system communicably coupled to the spatial light modulator to evaluate, using the processor, the one or more properties produced by the modified light at the distal end of the medium, generate a change to the variable mask that enhances the one or more properties of the modified light at the distal end of the medium, and provide feedback to the spatial light modulator to update the variable mask with the change identified by the control system. The control system generates the change to the variable mask using an optimization algorithm, a genetic algorithm, or machine learning to optimizes an objective function.

Embodiments of the present invention also include computer-readable storage media containing sets of instructions to cause one or more processors to perform the methods, variations of the methods, and other operations described herein.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings in which.

Figure 1A:
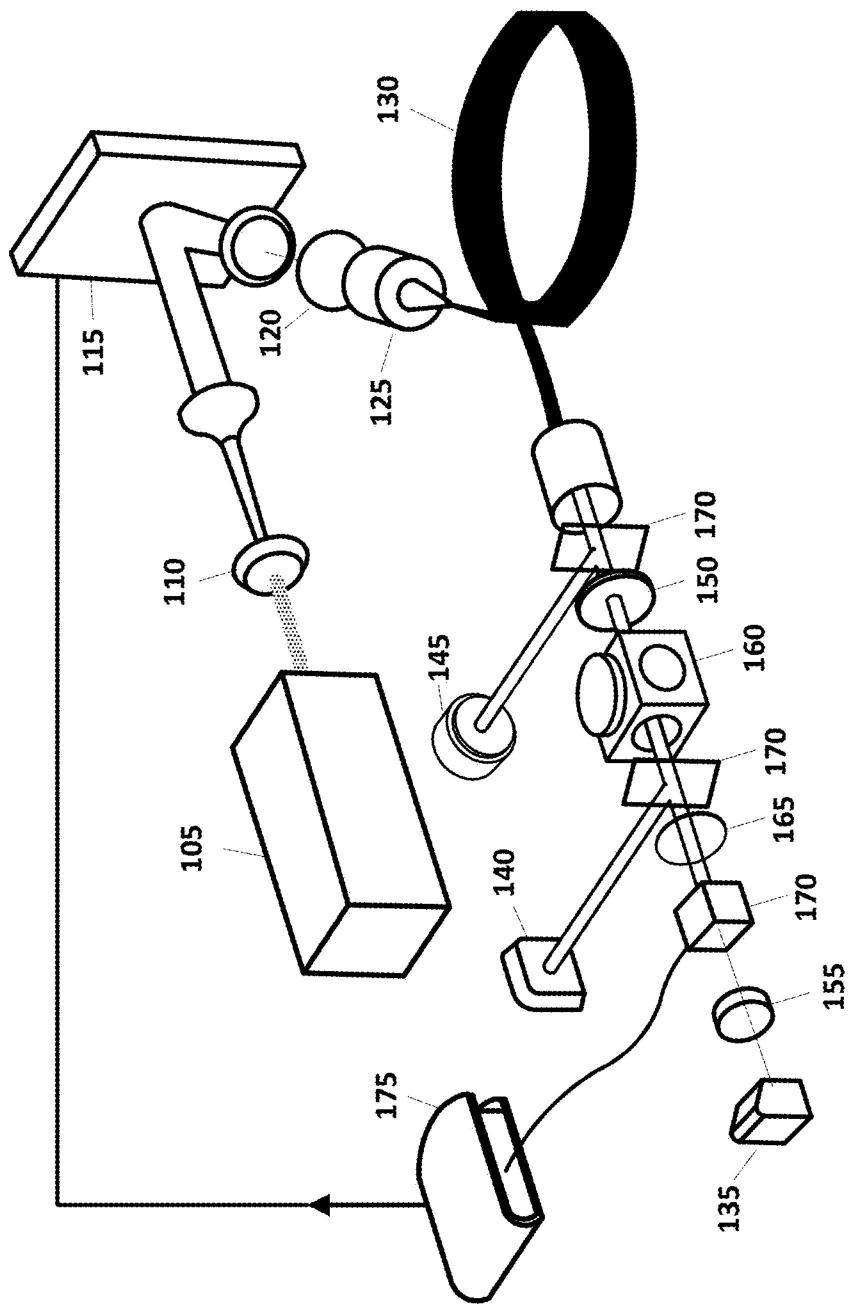
FIG. 1A illustrates an optical setup for wavefront shaping (WFS) control of nonlinear propagation in fibers in which some embodiments of the present technology may be utilized.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to wave-front shaping. More specifically, some embodiments of the present technology relate to wave-front shaping in nonlinear complex media such as waveguides, multicore fibers, or multimode fibers. Controlling light propagation through complex media is key in imaging and light energy delivery applications. In the last decade, a renewed interest in the topic was sparked by new fundamental discoveries as well as technological improvements in devices such as spatial light modulators (SLM) and computation capabilities. Accordingly, techniques for manipulating the wave-front incident onto the complex medium using high-resolution SLMs have helped mitigate scattering in random media and mode dispersion and coupling in multimode optical-fibers (MMF). Recent progress in the understanding of optical nonlinear media raises interest in nonlinear propagation for both fundamental and applied research. While nonlinear propagation in single-mode fibers has been thoroughly investigated, only sparse studies have addressed the richer nonlinear pulse propagation in MMFs, leaving this field largely unexplored with opportunities to exploit the multimodal degrees of freedom for controlling multi-dimensional spectral-spatio-temporal inter actions.

Single mode fibers have traditionally been adopted for most nonlinear applications due to the simplicity of their modal structure and propagation dynamics. However, multimode fibers are gaining new interest due to their potential as higher bandwidth waveguides for communication using space-division-multiplexing and high-power fiber lasers. In fiber lasers, the higher damage threshold of larger fibers is attractive as an alternative for power-limited single-mode fiber lasers and amplifiers. MMFs are important for endoscopic nonlinear microscopy and laser surgery, where nonlinear pulse distortions are expected. Recently, control over a variety of spatiotemporal nonlinear dynamics in graded-index (GRIN) MMF has been demonstrated by manually adjusting (laterally shifting) the input beam coupling to the fiber.

Various embodiments of the present technology introduce various systems and methods with wave-front shaping (WFS) to control nonlinear interactions using a SLM at the input coupling of the fiber. Using genetic algorithm (GA) based optimizations, some embodiments tailor and optimize the highly nonlinear generation of a stimulated Raman scattering (SRS) cascade and four wave mixing (FWM) in GRIN multimode fibers. Some embodiments allow enhancement, suppression and shifting of selected Stokes or anti-Stokes (FWM) peaks by WFS optimization of the mode-superposition at the fiber's input. It should be emphasized that the wave-front feedback control achieved with a SLM cannot be achieved with basic shifts of the laser spatial input coupling or alignment into the fiber.

Hence, WFS further provides a systematic approach for controlling and monitoring the complex dynamics of nonlinear phenomena in MMF. Various embodiments of the GA optimization present a solution to the inverse problem seeking to find the superposition of modes that enhances or suppresses specific nonlinear process. Remarkably, because the process is implemented experimentally online, various embodiments of the process can inherently take into account all optical system aberrations, misalignments, and fiber actual configurations. Other optimization algorithms are possible including gradient descent and simulated annealing. Further, machine learning processes are also applicable as a means to learn the response of the complex medium. Neural network approaches including convolutional neural networks and reservoir computing can be implemented as well within this framework.

The techniques described herein are also applicable for any guiding medium, including waveguides, multicore fibers, scattering media, waveguide arrays, and even bulk materials. Any among these media can be characterized by their linear and nonlinearly generated modes and hence the proposed systems and methods are applicable.

Various embodiments of the present technology provide for a wide range of technical effects, advantages, and/or improvements to computing systems and components. For example, various embodiments include one or more of the following technical effects, advantages, and/or improvements: 1) characterizing and controlling rich spatiotemporal dynamics in MMF; 2) application of WFS to nonlinear frequency generation, high power MMF lasers, nonlinear endoscopy, and nonlinearity suppression in multimode-fibers; 3) suppression of nonlinearities to improve system performance; 4) and an adaptive system with feedback control to suppress (or eliminate) nonlinearities in a multimode fiber link or other complex medium; and/or 5) providing a hardware basis for a neural network implementation.

For example, nonlinear suppression is critical for fiber optical communications. Nonlinearities limit the capacity of these systems. An adaptive system with feedback implemented in a multimode fiber link can reduce if not eliminate nonlinearities.

Some embodiments provide for a system to transmit information that would use multiple modes to avoid nonlinearity. The number of channels for communication being lower than the total number of modes of the fiber. These communication channels can be modulated with one of the usual techniques used in optical fiber communication such as amplitude/phase/polarization shift keying, quadrature amplitude modulation, m-ary pulse amplitude modulation, multilevel coded modulation. Further, multiplexing can be done in frequency or time.

Various embodiments may also be combined with Multiple Input Multiple output (MIMO) techniques, which exploit the spatial diversity of the multiple paths in multimode fibers, multi-core fibers, and fiber arrays.

Multiple communication channels can be implemented, each composed of several modes, in such a way that all together still do not produce nonlinear effects. There are fewer such 'forcefully linear' communication channels than the total number of modes of the fiber. The adaptive feedback system can take care of the random coupling in the (long) fiber while simultaneously ensuring the energy that leaks into unused modes remains negligibly small. Several figures of merit can be considered such as minimizing nonlinearities or communication specific metrics such as the symbol error rate. The use of WFS thus can enable higher transmission rates by avoiding the onset of nonlinearities in the fiber.

Another application of the system is in the implementation of a neural network. As such the modes of the fiber act as interconnection channels and the adaptive optimization produces a training of the interconnection weights implemented by the spatial light modulator. Neurons and synapses are implemented by the fiber modes and their linear and nonlinear coupling.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

Propagation of light in MMFs comprises a superposition of discrete propagating modes. Phase-velocity mode dispersion is aggravated by random mode coupling arising from imperfections and bends. They all contribute to creating complex 3D interference patterns, which result in a random speckle field at the fiber's output. Linear WFS techniques are based on an optimization of the input wave-front, an experimental determination of the optical transmission matrix, or on direct phase conjugation. Linearity of the system is a basic assumption in the transmission matrix formalism. In contrast to traditional systems, various embodiments of the present technology provide WFS that is used in the nonlinear regime where the transmission matrix formalism is not directly applicable. The nonlinear propagation is complex and cannot be described as a linear super-position of uncoupled modes. Nevertheless, various embodiments of the GA based WFS strategy is appropriate for nonlinear systems as shown below.

FIG. 1A illustrates an optical setup 100 for wave-front shaping (WFS) control of nonlinear propagation in fibers in which some embodiments of the present technology may be utilized. As illustrated in FIG. 1A, optical setup 100 can include a laser source 105, beam expander 110, spatial light modulator 115, 4f system 120, microscope objective 125, fiber 130, near field camera 135, far field camera 140, photodetector 145, notch filter 150, tunable ND filter attenuation 155, bandpass filters 160, lens 165, beam splitters 170, and spectrometer 175. The laser source 105 can be a nanosecond laser directed to SLM 115 through beam expander 110. SLM 115 can modulate the light coupled into MMF 115, and spectrometer 175 can provide feedback to the computer (not shown) controlling the SLM 115.

Laser source 105 may be a laser with 532 nm, ~7 ns pulses, energy up to 150 μJ and repetition rate of 20 KHz. Wave-front shaping can be performed using a liquid crystal spatial light modulator (LC-SLM) 115 (e.g., a Meadowlark 512×512) in some embodiments. Reflected light of the SLM 115 can be imaged by a 4f system 120 onto the back aperture of a microscope objective 125 (e.g., an Olympus, 0.14 NA or Leica 0.25 NA) that couples the light into the MMF 130. In accordance with various embodiments, MMF 130 may be an off-the-shelf GRIN fiber (e.g., Corning, 62.5/125-μm) with changing lengths in the range of 2.65 m-1 Km, a 100 m, 62.5/125-μm fiber (e.g., Thorlabs GIF625), step-index fiber (e.g., Thorlabs FG0S0LGA), or other medium as appropriate for the application.

The fiber output can be coupled into a customized microscope for near and far-field imaging (e.g., using near field camera 135 and/or far field camera 140) of fiber modes with the possibility to switch between different optical configurations. The microscope can include output power monitoring, notch filter 150 (e.g., Thorlabs NF533-17), tunable ND filter attenuation 155, and a series of narrow band pass filters 160. The anti-Stock bands can be analyzed using a short-pass filter (e.g., Semrock BPS0I-532-25) to avoid saturation of the detector due to the intense SRS. For parallel spectral detection, the light beam was split and coupled into a multimode-fiber to average the spectrum in space and from there coupled into spectrometer 175 (e.g., OceanOptics Flame VIS-NIR or NIR-512).

The signal from spectrometer 175 can acquired and analyzed by a computer (not shown). In some embodiments, the SLM 115 can be divided into independent macro-pixels with phases varying between 0 and 2π. A genetic algorithm (GA) can be used to optimize the values of each macro-pixel based on a merit function tailored to the application. Accordingly, merit function can be adjusted to characterize a specific spectral feature, which can be recorded at the output tip of the fiber and fed back to the computer or processor. The GA can process start with a set of random phase patterns and iteratively converge to an optimized phase mask that enhances the selected spectral feature.

SRS cascade generation is an important nonlinear process that builds up throughout the fiber from spontaneous Raman scattering. Phase matching for SRS is satisfied throughout the fiber since the medium is actively participating in the interaction in the sense that the process depends on lattice-vibrations of the fiber. The Raman gain, $g_R$, for fused silica is maximal at 13.2 THz (440 $cm^{-1}$), and therefore, the first Stokes line, at 440 $cm^{-1}$, builds up most rapidly once the power reaches the SRS threshold, and the energy is transferred from the pump to the Stokes wave. For sufficiently large input laser pulse power, before all the energy is transferred, the Stokes wave itself serves as a pump to generate a second order Stokes wave. If its power becomes strong enough, this process can generate a cascade SRS of multiple Stokes bands with its order increasing with fiber-length. SRS cascades can be demonstrated first using single mode and small-core fibers, and later on using large core MMF and highly customized fibers.

Considering single mode propagation, the number of Stokes bands depends primarily on the input power. In MMFs the spatial overlap integral of the pump and Stokes along the fiber determines the efficiency of the interaction for a given input power. Stokes waves can evolve into one of the low-order modes or a combination of these modes under suitable light launching conditions and the efficiency of the process for a particular mode depends on the coupling efficiency of the pump into the individual mode.

Four wave mixing (FWM) is another dominant phenomenon that interplays with SRS in MMFs. It is a $X^3$ parametric nonlinear process that involves the interaction of four optical waves. Two pump waves annihilate to produce Stokes and anti-Stokes (frequency up shifted) photons. Here the medium plays a catalytic role and optical momentum conservation is required before nonlinearities can build up. In single mode fibers, there are several techniques for achieving phase matching. However, the presence of multiple propagating modes in MMFs, each of them having different dispersive properties and corresponding momenta, results in expanded phase-matching combinations for the generation of FWM signals.

The WFS control of the interplay between SRS and FWM is the major phenomenon controlled in various embodiments. In long fibers, SRS practically dominates the interaction because it is difficult to maintain phase matching over long fiber lengths. In shorter fibers, the phase matching condition in MMF can be satisfied for several combinations of the fiber modes. As such, the multimode nature of these fibers presents numerous additional opportunities for exploiting modal-phase-matching to enhance nonlinear interactions that historically remained unexplored.

Figure 1B:
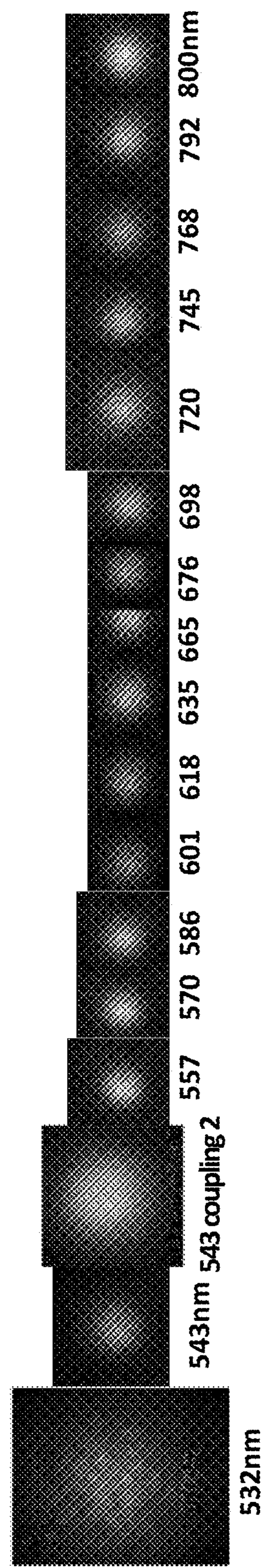
FIG. 1B illustrates near field imaging in an SRS cascade in a MMF.

In order to illustrate the richness of phenomena, some embodiments used in various experiments launched 532 nm ns pulses into a GRIN MMF 130. Remarkably, the SRS-FWM cascade generated extends from 470 nm up to 1700 nm (the limit of our detection) and possibly beyond; with all the peaks undergoing mode cleaning (see near-field images in FIG. 1B), e.g., they contain low order modes rather than the typical speckle fields of linear MMF. The generated cascade is stable with fiber movement and the stability increases with fiber length. This simple MMF system produces a highly nonlinear, tunable, multiple frequency single-mode source, that can be used for various application. As such, various embodiments influence of the input wavefront on the generated nonlinear phenomena.

Figure 1C:
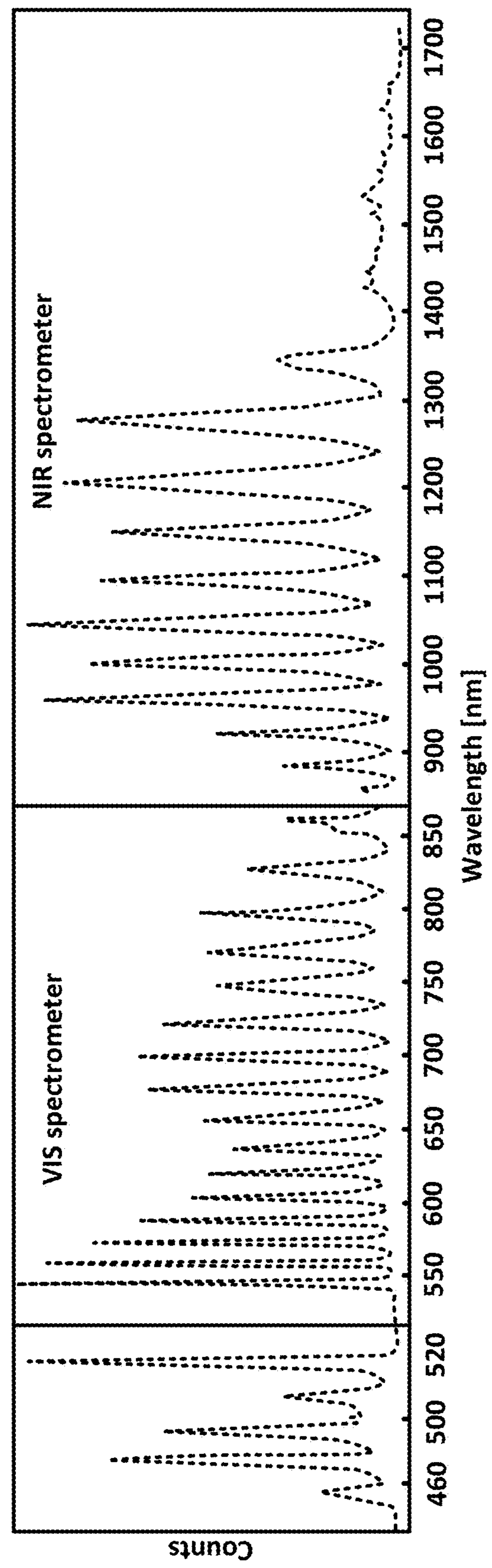
FIG. 1C shows the spectrum of an SRS-FWM cascade in 1 Km GRIN MMF.

FIG. 1C shows the spectrum of an SRS-FWM cascade in 1 Km GRIN MMF. Anti-Stokes peaks were recorded using an additional short pass filter. The filtering and integration time in the three regions of the spectrum were varied for representation. Pulse energy ~50 μJ and a repetition rate of 20 KHz.

In a first experiment, the enhancement of FWM interaction in short fibers was investigated. Using WFS, the intensity (maximum of the peak count value) of the first FWM anti-Stokes line at 517 nm was optimized. The anti-Stokes side of the spectrum that contains only FWM peaks without the SRS peaks that dominate the Stokes side was analyzed. The optimized SLM phase shows significant (six-fold) enhancement in the peak intensity compared to a flat phase at optimal mechanical focus alignment, a reference case in which the SLM serves as a mirror and the manual coupling maximizes the peak (FIG. 2).

In the comparison, the input energy is kept constant and the flat phase spectra is measured before and after optimization to validate mechanical and thermal stability. The WFS optimization rises up sharply, at a certain threshold, reflecting the nonlinear nature of the feedback. Interestingly, the FWM anti-Stokes peak propagates as a $LP_{21}$ mode (FIG. 2C), completely different than the pump (multimode) and Stokes waves (mostly $LP_{01}$). Here the WFS optimization maximizes the FWM by launching a phased matched combination of pump modes.

Figure 2A:
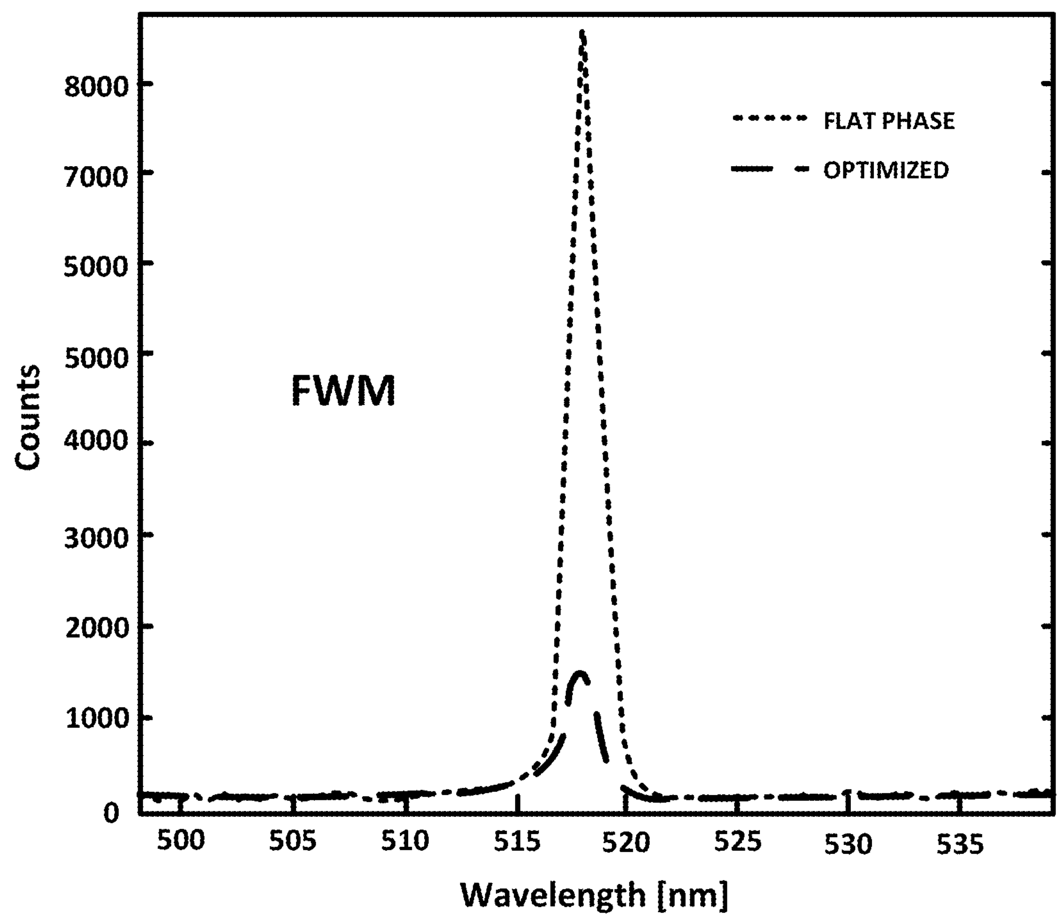
FIGS. 2A-2F illustrates a reference case in which the SLM serves as a mirror and the manual coupling maximizes the peak.
Figure 2B:
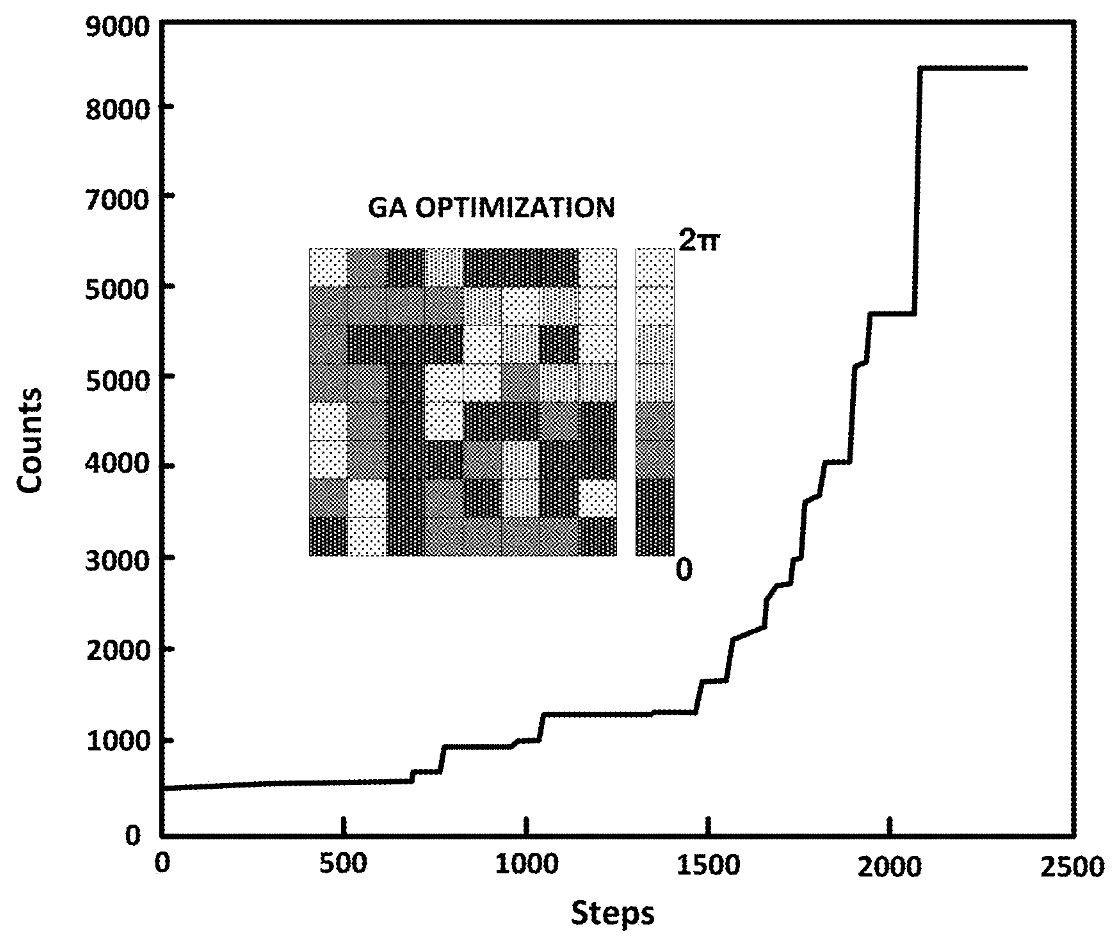
Figure 2C:
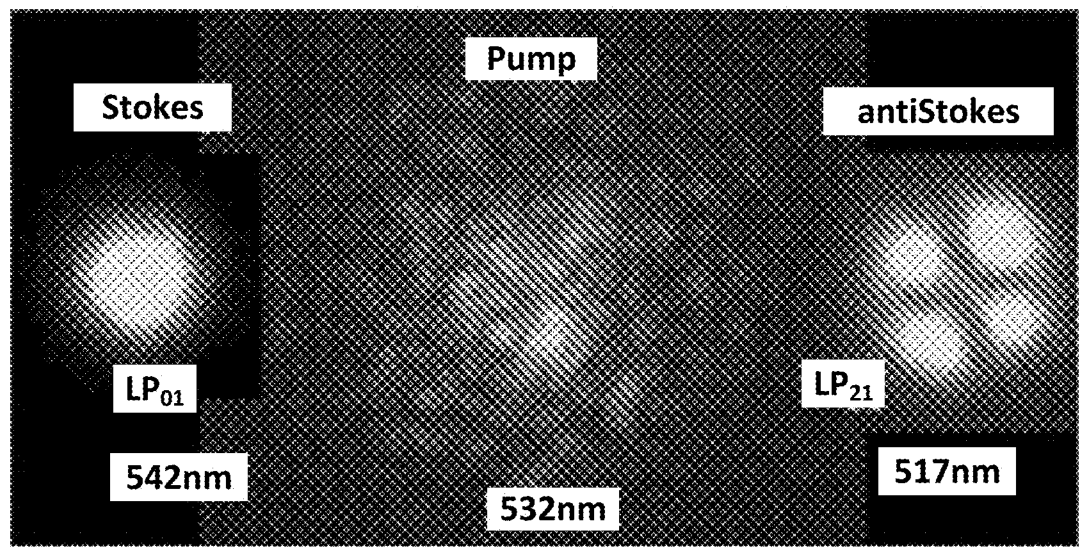
Figure 2D:
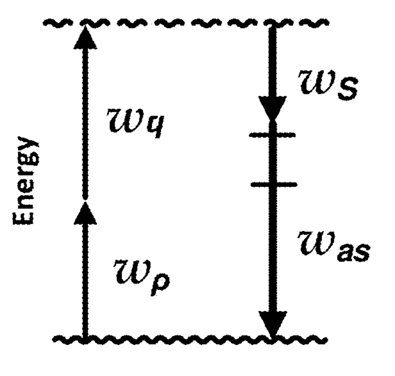
Figure 2E:
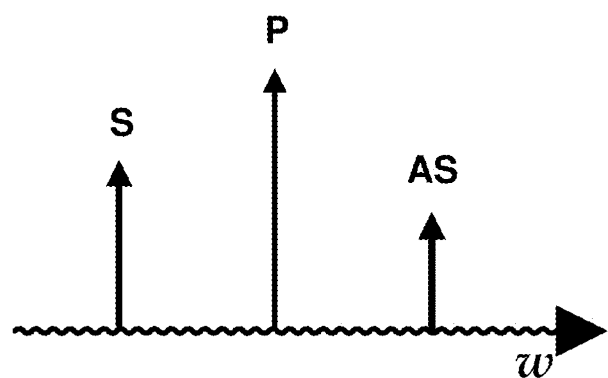
Figure 2F:
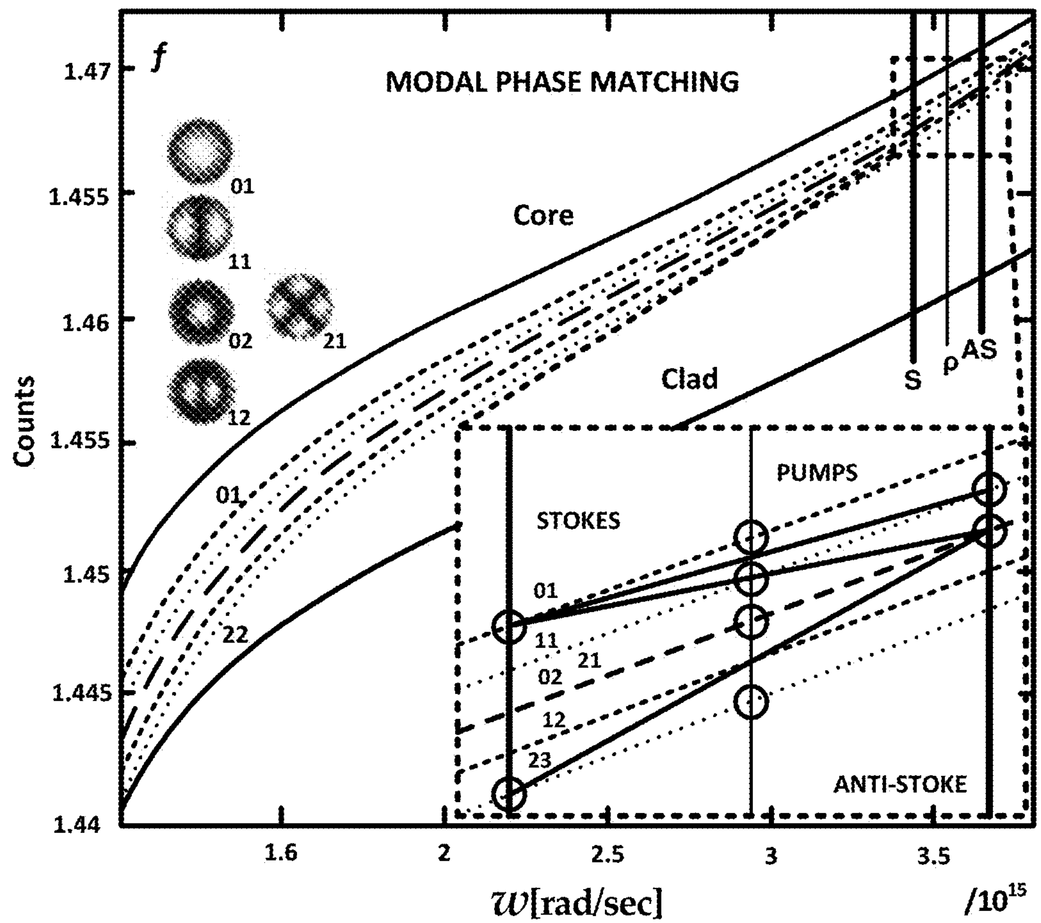

FIGS. 2A-2E illustrates a reference case in which the SLM serves as a mirror and the manual coupling maximizes the peak. In FIG. 2A, an enhancement of FWM peak at 517 nm is illustrated. The 2.65 m GRIN fiber was stretched in an aluminum v-grove rail and thermally stabilized in water-based gel. The optimization process is illustrated in FIG. 2B. Maximal values at each step of the GA algorithm are depicted in FIG. 2B. The insert shows the optimal phase patter. A 0.14 NA objective was used with a pulse energy of 32 μJ. In FIG. 2C, a nearfield image of the Stokes, pump, and anti-Stokes peaks at the fiber output are illustrated. In FIGS. 2D and 2E, FWM energy and spectrum schemes are illustrated. In FIG. 2F, a simulation of intermodal-phase-matching is illustrated. The material refractive-index is plotted including material dispersion. Several modes in the GRIN fiber are also shown. The bottom right insert is zoom-in on the experiment regime. The other lines denote Stokes(S), Pump (P), and anti-Stokes (AS) wavelengths, intersecting with the calculated modes, and indicating possible propagation waves. The allowed phase-matched combinations are also illustrated. The two corresponding pumps are marked with black circles and connecting curves. For each phase-matched process, the pumps average falls on the crossing of the line and pumps spectral line.

A simulation of the material refractive-index of modes in GRIN fibers describes the mechanism of intermodal-phase-matching (FIG. 2F). Accordingly, the observed FWM peaks could be created by pump waves that satisfy the phase matching condition, $$\Delta\beta=\beta_{01}^{s}+\beta_{21}^{as}-\beta_{lm}^{p}-\beta_{l'm'}^{p'}=0$$

where $\beta_g^{wave}=n_{eff}k_0$ is the propagation constant of the modal-group-number, $g=|l|+2m+1$, and its k-vector. The index wave indicates either pump (p), Stokes (s) or Anti-Stokes (as). The optimized 532 nm pump wave is highly multimode as indicated by its speckle pattern at the output and the WFS optimization maximizes the launching of phase-matched pump modes at the input. Note that a single mode pump at $LP_{01}$ cannot produce a $LP_{21}$ anti-Stokes with $LP_{01}$ Stokes mode through the phase-matched process. Such a combination also violates angular momentum conservation (supplementary-materials). Therefore, it is evident that the pump comprises higher order modes and, upon optimization, the SLM launches efficiently a combination of phased-matched modes into the fiber, systematically surpassing what is possible with manual coupling. The mechanism for phase-matching could include additional nonlinear effects, generating additional momenta along the GRIN fiber. The complexity of these nonlinear interactions highlights the advantages of WFS optimization that accounts for all the dynamically-rich effects for a desired response.

Next, the Stokes side of the spectrum was investigated with the goal of enhancing the SRS cascade in a 100 m GRIN fiber. The GA optimization merit function was set for the enhancement of a selected spectral region of interest. FIG. 3 depicts the SLM control over of the cascade as the nonlinear interaction in the MMF were selectively tuned.

Figure 3A:
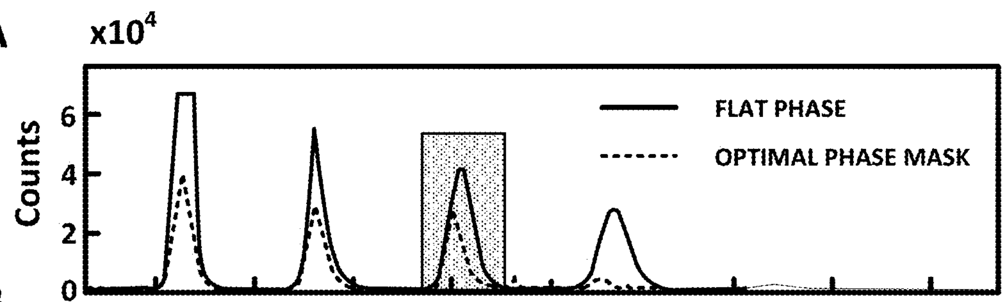
FIGS. 3A-3D illustrate wavefront shaping of SRS peaks according to one or more embodiments of the present technology.
Figure 3B:
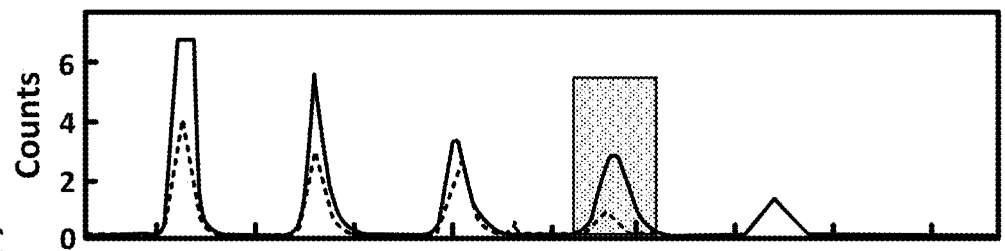
Figure 3C:
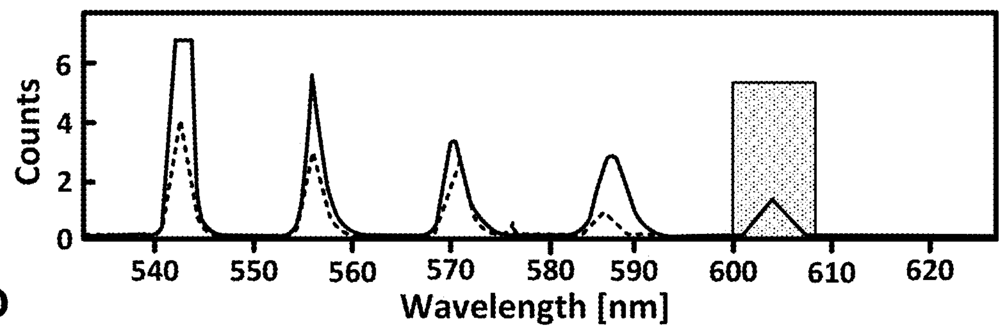

In FIG. 3A-3C, the 3rd SRS, 4th SRS, and 5th SRS peak optimization results are illustrated. The square marks the spectral region of interest for each optimization. In each plot, a flat phase on the SLM is compared to the optimal phase mask. The input energy was kept constant for comparison. A 0.14 NA objective was used with a pulse energy of 18 μJ.

Figure 3D:
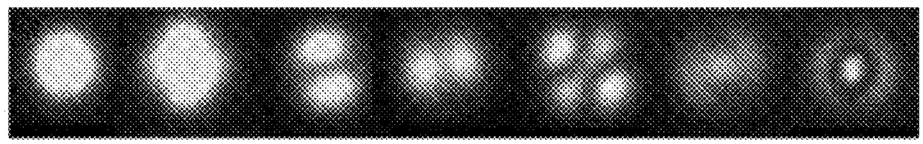

The SRS cascade can be generated in several low order modes, as depicted in the near-field images of SRS 543 nm peak modes in a 20 m GRIN fiber as shown in FIG. 3D. However, the most efficient cascade is generated once the fundamental mode is excited. In this case, the mode-cleaned pump overlaps spatially with the generated Stokes wave and the cascade keeps generating clean fundamental modes of higher wavelengths. The SLM optimizes the input superposition of modes for fundamental mode excitation, compensates for aberrations in the optical system, and enables dynamic feedback monitoring on the SRS cascade.

In terms of the modal control, the optimization of the SRS cascade efficiency is a rather simple example because it does not include complex modal excitation. On the other hand, the SRS interplay with FWM illustrates more complex intermodal phase matching. Such is the case in the next experiment where an SRS cascade was generated in a 1 km long GRIN MMF and demonstrate spectral shifting of each peak of the cascade. The spectral shifts occur as the input excitation of the fiber is continually tuned from the optimized fundamental mode (longer SRS wavelengths) to a mixed mode excitation (SRS wavelengths downshift). At mixed modal excitation, the interplay of FWM becomes dominant and mediates the SRS cascade. For this experiment, the WFS figure of merit function was defined as the weighted average wavelength location in a selected spectral ROI as follows:

$$\lambda_{merit}=\lambda_{ref}\pm\frac{\int_{\lambda_1}^{\lambda_2}\lambda_n * I_{SRS_n}}{\int_{\lambda_1}^{\lambda_2}\lambda_n},$$

where $\lambda_1$ and $\lambda_2$ define the spectral ROI, $I_{SRS}$ is the spectrum intensity and ±defines the wavelength shift direction with respect to a reference, $\lambda_{ref}$. The SLM provides continuous control over the spectrum to produce the desired output by controlling the mixture of modes at the input of the MMF.

The spectral shifts of the cascade are obtained by mixed-mode excitation. Here, the GA provides an optimized collection of modes on the SLM that generates a selective FWM interaction to pull the average wavelength down. Similar spectral-shifts can be achieved by manually adjusting the input coupling of the fiber. However, the SLM provides a systematic and controlled feedback methodology that allows precise modal excitation for the desired results.

Figure 4A:
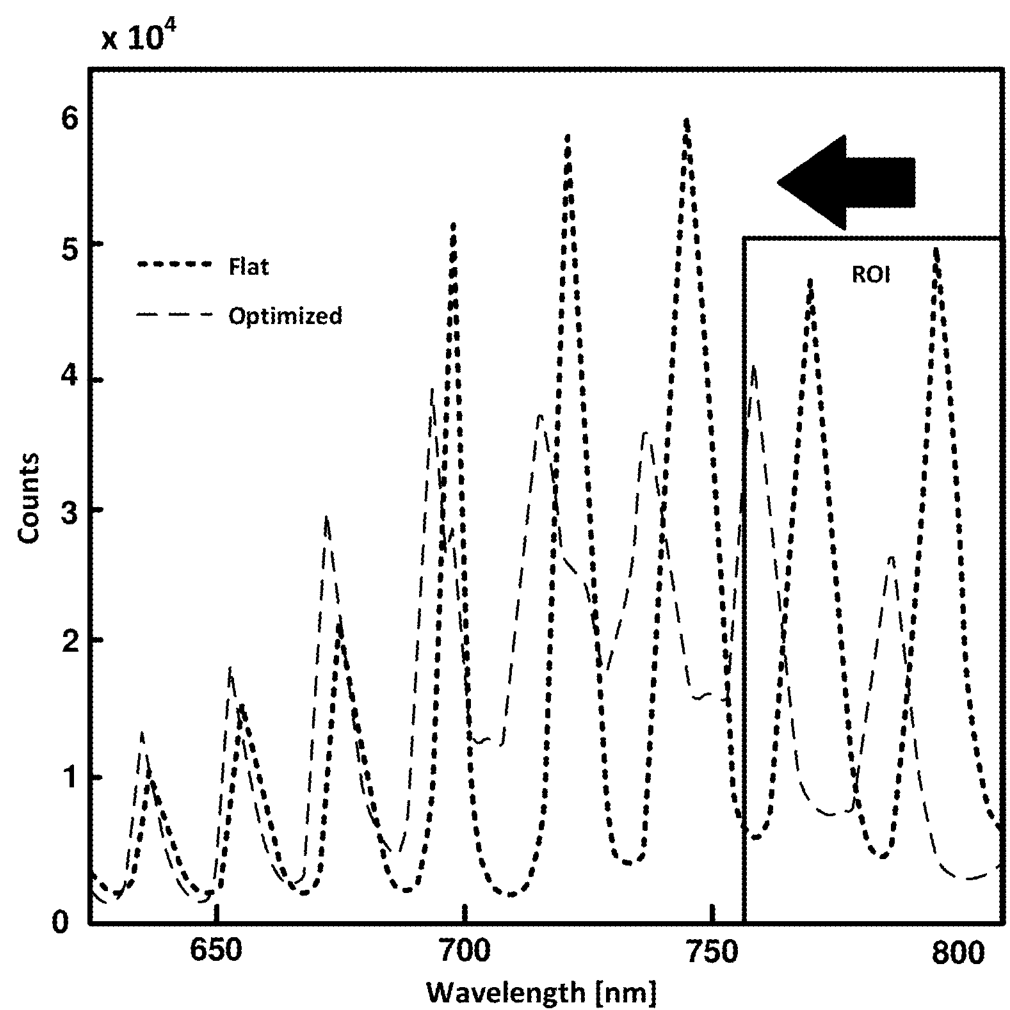
FIGS. 4A-4B illustrate wavefront shaping of spectral shifts according to one or more embodiments of the present technology.
Figure 4B:
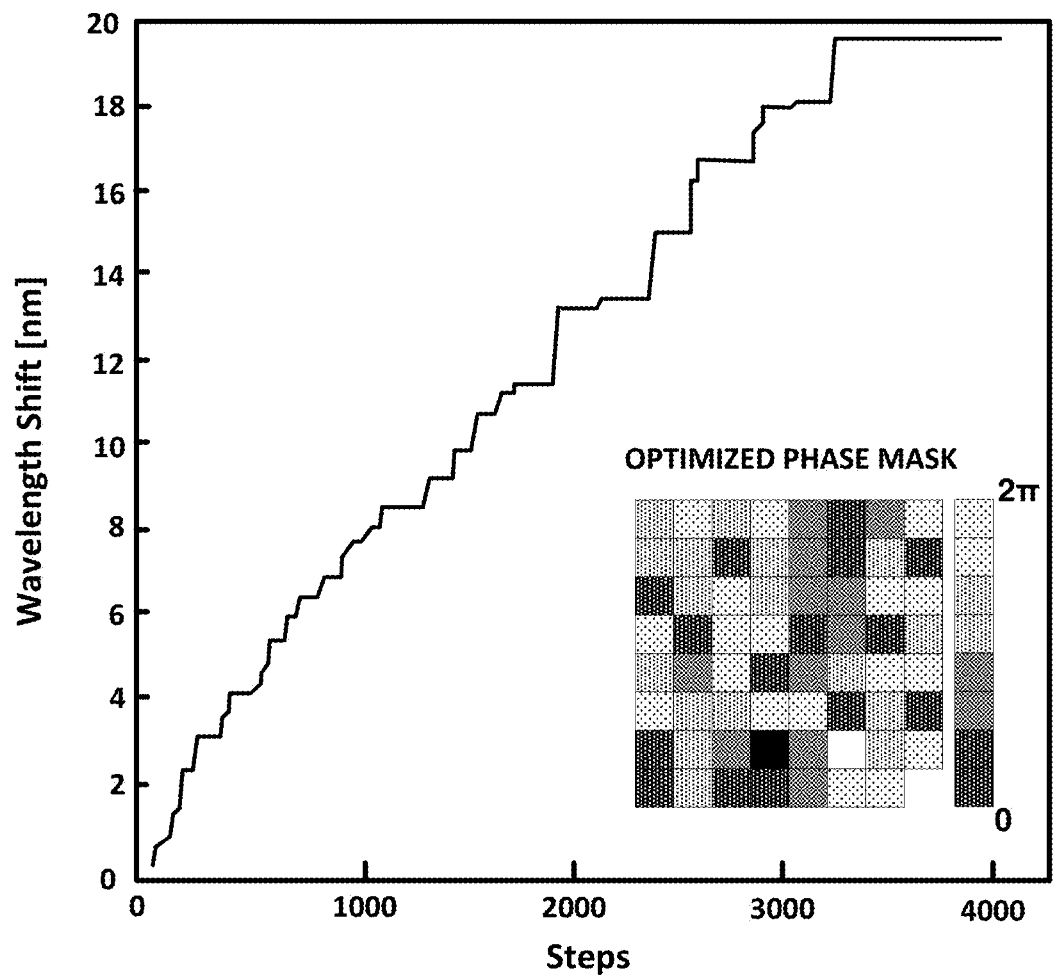

FIGS. 4A-4B illustrate wavefront shaping of spectral shifts according to one or more embodiments of the present technology. FIG. 4A represents the optimization of shifts towards lower wavelength and mixed mode excitation. The GA optimization process generated shifts of up to 20 nm. The spectrum is continually shifted with the excitation of higher order modes that supported FWM processes along the SRS cascade. The rectangle shows the selected spectral region of interest. In FIG. 4B, the plot shows the GA performance and the bottom-right insert depicts the optimized phase mask. A 0.14 NA objective was used with laser pulse energy of 50 μJ.

Figure 5A:
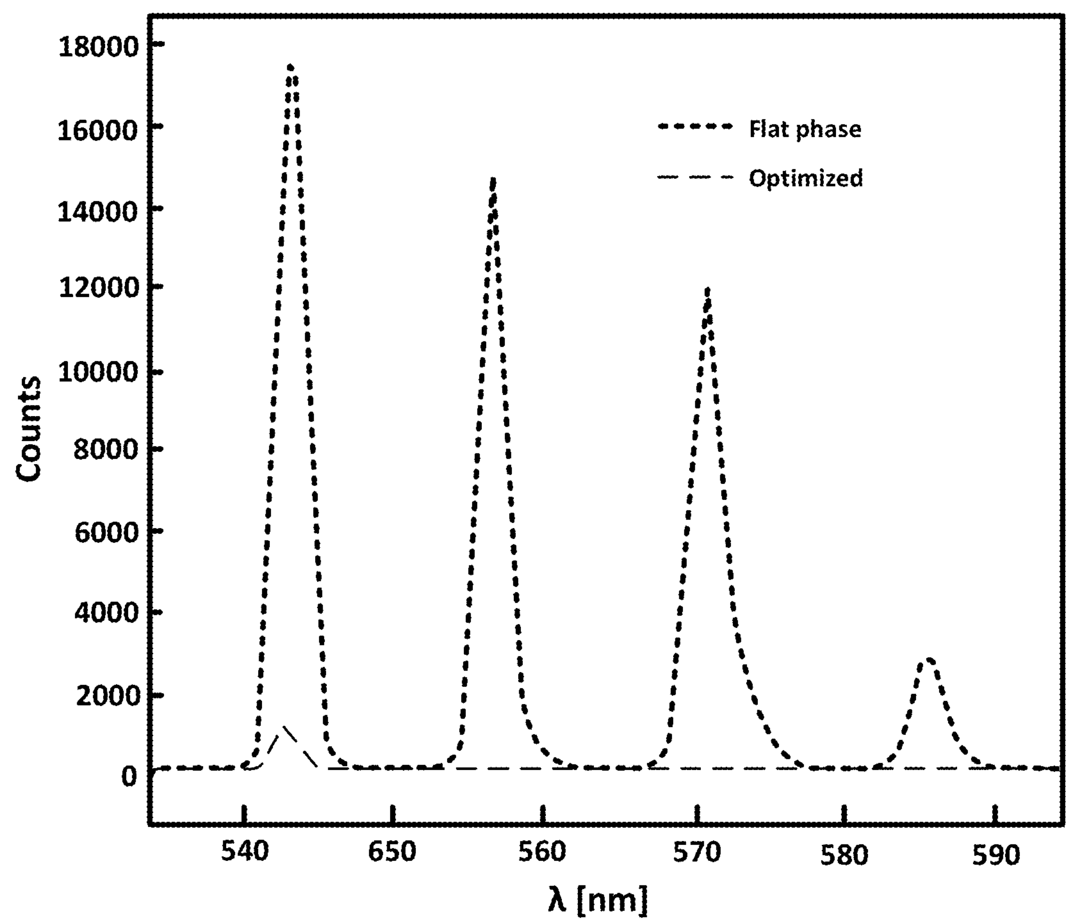
FIGS. 5A-5B illustrate an SRS cascade suppression through hide mode excitation in accordance with some embodiments of the present technology.

A tunable source based on nonlinear WFS control could be beneficial for various laser applications. However, for light-wave communications, nonlinearities limit the information capacity of fiber networks. Suppression of nonlinearity is therefore highly desirable for the constantly growing bandwidth demand. In FIGS. 5A-4B suppression of the SRS cascade in a 1 Km GRIN fiber is demonstrated. The suppression feedback figure-of-merit, $F_{merit}$, comprises two components: the total energy of the SRS cascade, $I_{SRS}$, and the total transmission in the fiber as follows:

$$F_{merit} = \frac{1}{2}\left(\frac{\int_{\lambda_1}^{\lambda_2} I_{SRS(ref)}}{\int_{\lambda_1}^{\lambda_2} I_{SRS}} + \frac{I_{out}}{I_{out(ref)}}\right),$$

where $\lambda_1$ and $\lambda_2$ are the spectral limits of the ROI. $I_{SRS}$ appears inverted and normalized, while $I_{out}$ is normalized. The fiber transmission, $I_{out}$, is measured at the output before spectral filtering and its place in the figure-of-merit assures that the suppression of SRS is the result of high-mode excitation and not simply decoupling of light by diffraction on the SLM. For simplicity, some embodiments may weight the two optimization components equally, but it is possible to choose a different weighting function In addition, the total transmission was measured before and after optimization to normalize any diffraction effects in the suppression experiment. After optimization, the projected phase pattern decreased the total transmission by 10%, compared to an averaged random-phase (initial mask in the GA process) and by 66%, compared to the flat-phase-transmission. In the flat-phase comparison of FIG. 5A, the laser energy was reduced by 66%, compared to the power used in the optimization, and plotted the flat-phase output with identical total transmission to the optimized-phase mask. The optimization of the embodiments used suppressed the SRS cascade by a factor of ×52. This value represents the ratio of the integrated SRS cascade spectra for the normalized flat-phase and optimized-phase cases.

Figure 5B:
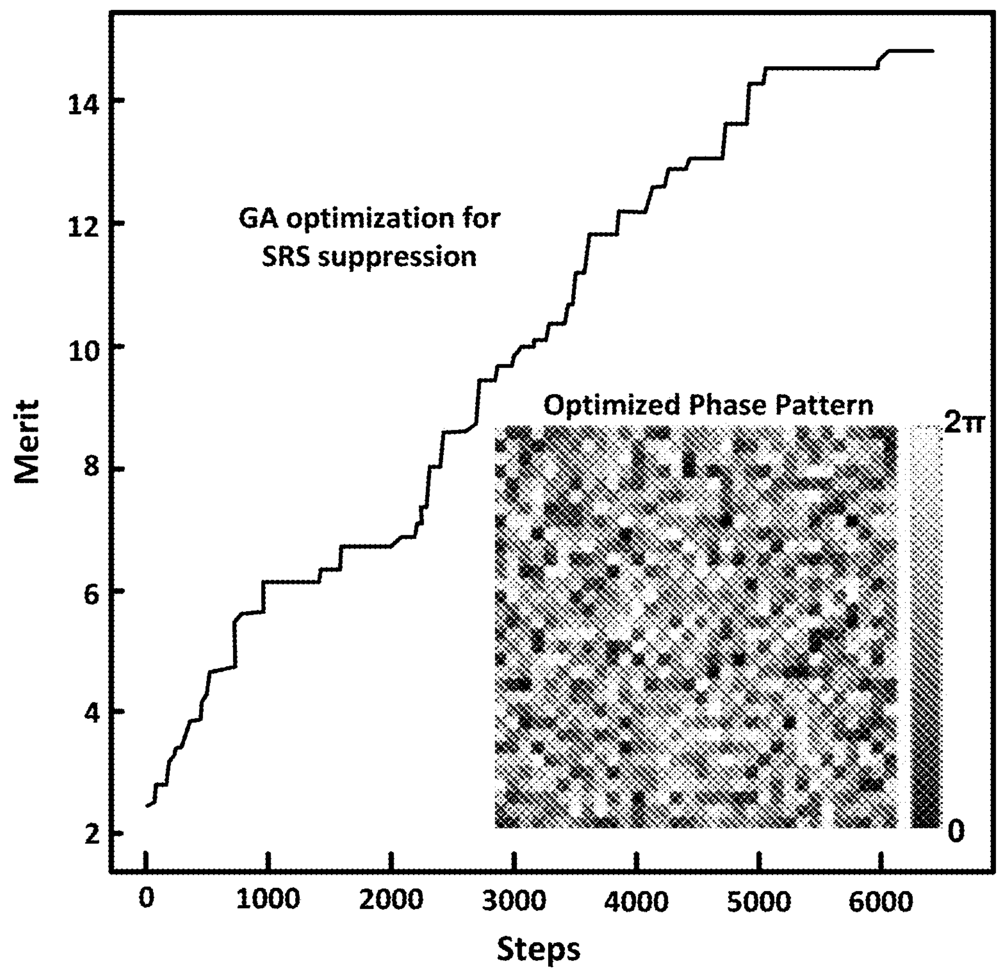

FIG. 5B shows the WFS enhancement of the figure-of-merit with iteration number. The dramatic, ×7, suppression of the SRS cascade from the initial random pattern shows that optimizing the higher order mode superposition is significantly more effective than a non-optimized speckle pattern, such as could be achieved with a simple NA-matched diffuser.

The WFS control of various nonlinear processes used in various embodiments enables spectral shaping via the coupled spatial modal control. Generally, as the fibers get shorter, the effect of WFS becomes more noticeable. Fiber cut-back experiments show that <50 m fibers support several SRS modes while in the longer fibers, mostly the fundamental clean mode appears, hinting that a mode competition occurs along the length of the fiber. Even with short fibers of <5 m, the most efficient SRS cascades occur once the fundamental mode is excited efficiently. While similar effects could also be achieved without a SLM, using an optimized lens coupling into the fundamental mode, WFS provides a controlled way for enhancing the mode excitation. Furthermore, WFS enables control over FWM, spectral shifting, and nonlinearities suppression by coupling a tailored superposition of modes into the fiber. All of these phenomena and capabilities are attained beyond the capabilities of simple lens-coupling.

GRIN fibers have unique properties for generating interesting nonlinear interactions not always shared by step-index fibers. For instance, step-index fibers (50 microns, 10 m) have been tested and could not attain SRS nor FWM with the maximal laser power.

The number of macro-pixels utilized in the SLM has to be carefully considered. Once phase patterns are displayed, some of the light is diffracted out of the fiber, reducing the coupled input power and decreasing the nonlinearity regardless of the particular modes excited. As the number of SLM macro-pixels increases, the diffraction spectrum broadens, further reducing the input power coupling. In order to limit this unwanted diffraction, the number of SLM macro-pixels was limited between 64-1024, and each phase pattern was slightly low-pass digitally filtered to smooth the phase edges. After taking into account the diffraction decoupling effects and strict criteria, namely a constant laser power for enhancement and a normalized coupling power into the fiber for suppression, as described above.

Thermal management plays an interesting role in the SRS cascade. For the WFS experiments, the coupling of thermal effects was the primary concern with optimization of the efficiency of nonlinearities. To eliminate thermal effects, some embodiments align a short fiber in an aluminum v-shaped profile and immersed the fiber in water-based gel. This configuration can allow for improved thermal management, and can be compared the flat phase spectrum before and after optimization to ensure that the thermal management keeps the fiber at the same conditions over time and during WFS. Note also that liquid-crystal SLMs and other phase modulators are subject to optical damage in high-power applications. Proper precautions ensure safe operation with a high-power ns laser.

The application of nonlinear MMF requires long term stability of the system. Using an active device in some embodiments, such as an SLM, allows degree of dynamic control that maintains operation over long periods of time compensating for mechanical and thermal drifts. Such techniques open up a new field of adaptive nonlinear optics. In moving forward and generalizing nonlinear WFS it is interesting to explore how WFS controls systems with different types of nonlinearity. Some experiments in a specific regime were evaluated: wavelength of 532 nm, normal dispersion in the fiber, and ns pulses where group-velocity-dispersion effects are of minor importance. Various embodiments provide several important applications of WFS control in nonlinear MMF including enhancement, shifting and suppression of SRS and FWM.

Various embodiments provide for WFS control and optimization of nonlinear interactions in MMF. By optimizing the input phase of the fiber-coupled wavefront, the energy of selected SRS and FWM peaks can be tuned creating a configurable source with tailored performance. The adaptive in-line optimization represents an approach to solve the nonlinear inverse problem of finding a tailored superposition of modes at the input of the fiber for a desired spectral output.

Genetic Algorithms

The GA optimization for WFS used in some embodiments can start with a population set of random phase masks (e.g., 30) and iteratively converges to an optimized pattern. At each step, a phase mask is displayed on the SLM and a merit signal is recorded, based on a specified spectral analysis at the fiber's output. The recorded values of the initial population are ranked based on the selected figure-of-merit and a new generation, containing new phase masks (e.g., 15 off-springs) is created. The breeding process combines two phase masks from the population, which are randomly chosen with a probability weighted by the ranking. At each step of the GA, a new phase mask can be displayed on the SLM and the corresponding figure-of-merit can be recorded. The ranking and breeding process repeats itself every cycle (e.g., 15 measurements), always keeping the highest ranked phase-masks (e.g., 30) as the population for the next iteration.

As a result, a phase mask can be found that enhances the selected figure-of-merit and corresponding spectral feature. The optimization time can be determined by the number of steps and the acquisition time. Typically, the spectrometer acquisition time can be set to 10 ms with additional ×3 averaging for each step. The SLM refresh time can also be in the order of 10 ms leading to approximately 50 ms per measurement. Accordingly, for ~10,000 measurements, the optimization times were in the order of 10 minutes using a non-optimized MATLAB software.

Modal Phase Matching

Efficient generation of nonlinear processes such as four-wave-mixing (FWM) requires minimal effective phase mismatch. In the degenerated four wave mixing process the bulk mismatch is defined as:

$$|\vec{k}_s+\vec{k}_a-\vec{k}_{P1}-\vec{k}_{P2}|=\Delta k,$$

where $\vec{k}_s$, $\vec{k}_a$, $\vec{k}_{p1}$, and $\vec{k}_{p2}$ are the wave vectors of the anti-Stokes, Stokes, and pumps. In the GRIN fiber, each wave-vector is slightly reduced compared to its value in the bulk material at the fiber core. To express the mode-dependent momentum, the propagation constant $\beta_{lm}$•is related. The mode and frequency-dependent propagation constant can be calculated by solving the propagation equation of modes. In a GRIN fiber, $\beta_{lm}$ can be analytically approximated as $$\beta_{lm} \approx n_1 k_0 \left[1 - 2\left(\frac{g}{m}\right)^{\frac{\alpha}{\alpha+2}} \Delta\right]^{\frac{1}{2}},$$

where α is the graded profile parameter that is typically between 1.8 and 2.2, g is the modal group number and $$M = \frac{\alpha}{\alpha+2} n_1^2 k_o^2 R^2 \Delta$$

is the total number of modes in the fiber. $n_1$ is the peak refractive index difference between at the core and the clad. R is the core radius and $$\Delta = \frac{n_{cor} - n_{clad}}{n_{cor}}$$

is the normalized refractive index difference between the core and the clad. The equivalent phase mismatch in a MMF, based on modal phase matching mechanism, is defined as $$\Delta\beta = \beta_{l_s m_s}{}^{s} + \beta_{l_a m_a}{}^{as} - \beta_{l_1 m_1}{}^{P1} - \beta_{l_2 m_2}{}^{P2},$$

where $\beta_{lm}{}^{wave}$ is the propagation constant of a wave with mode l, m (angular, radial), presented as linear polarized base, $LP_{lm}$, and effective FWM requires $\Delta\beta \cong 0$. The effective refractive index of a mode is given by:

$$n_{eff}^{lm} = \frac{\beta_{lm}}{k_0}.$$

A three term Sellmeier dispersion equation was used for the refractive index $$n^2(\lambda) = 1 + \sum_{i=1}^{3} \frac{a_i \lambda^2}{\lambda^2 - b_i},$$

where λ is the wavelength, n(λ) is the refractive index and $a_i$, $b_i$ are the fitting parameters. The effective index diagram depicts the GRIN mode groups as a function of the radial frequency ω. Compared to the equivalent $\beta_{lm}(\omega)$ diagram, the refractive index diagram highlights the material dispersion that is compensated via modal phase matching. Therefore, the require phase-matching conditions on the refractive index diagram are illustrated. Note that $$\beta_{lm} = n_{lm}(\omega)\frac{\omega}{c}$$

Is a direct representation of the momentum and appropriate for phase-matching calculations.

Figure 6A:
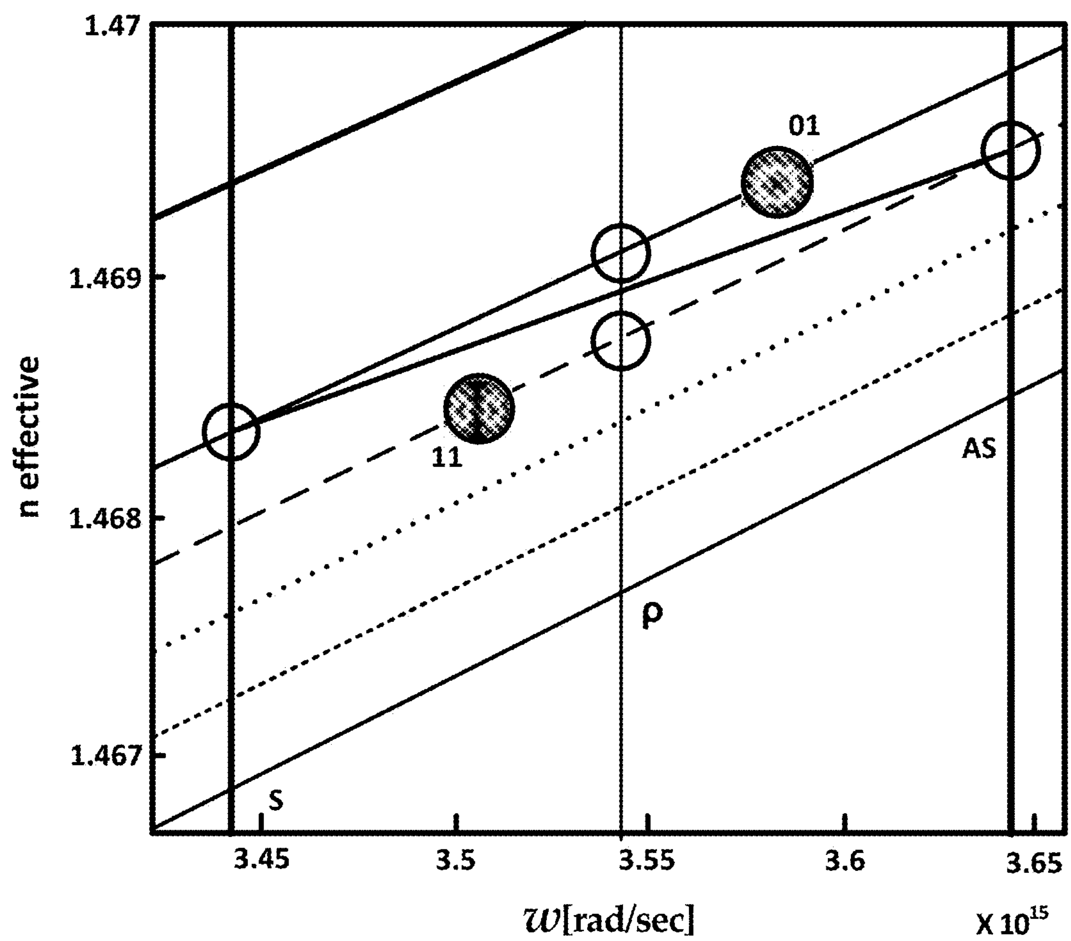
FIGS. 6A-6C illustrate a simulation of intermodal-phase matching in accordance with one or more embodiments of the present technology.
Figure 6B:
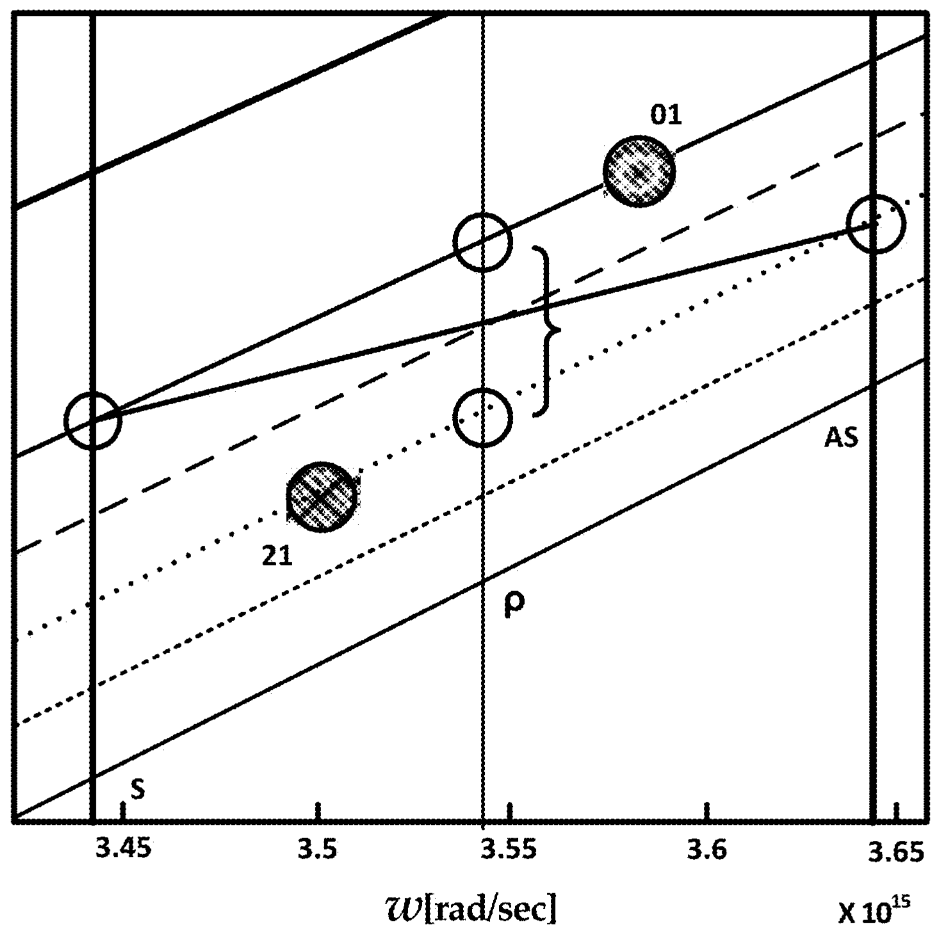
Figure 6C:
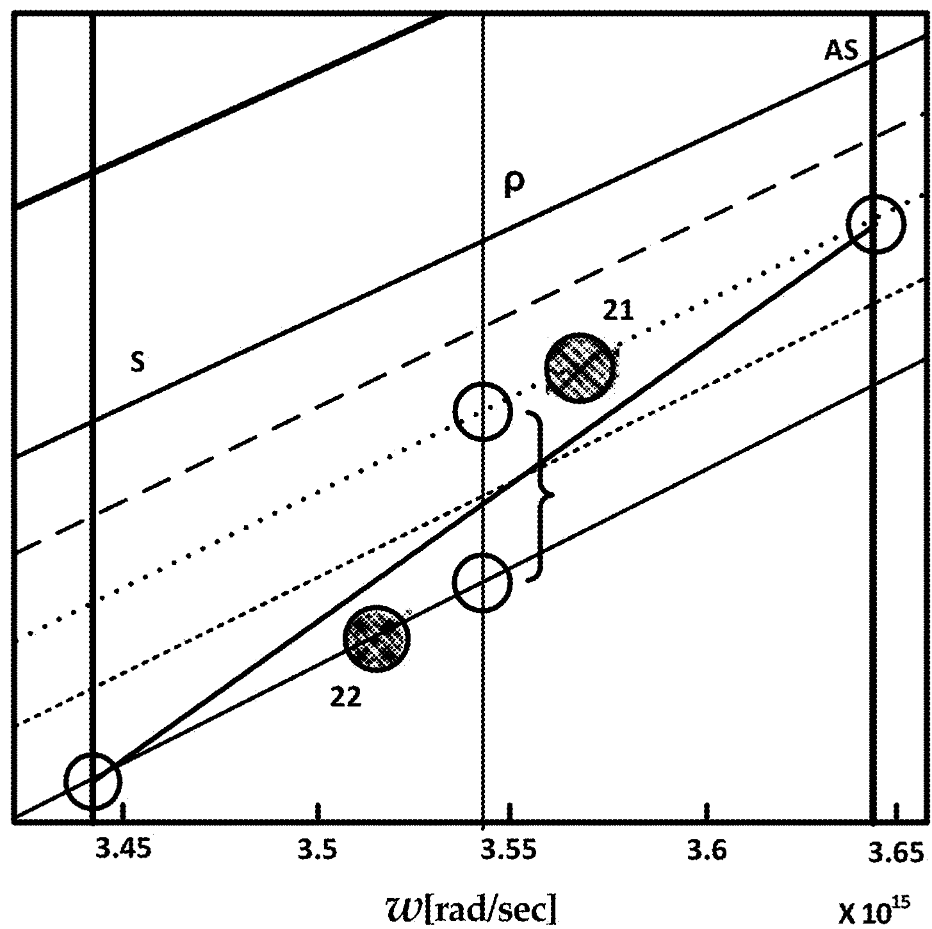
Figure 7:
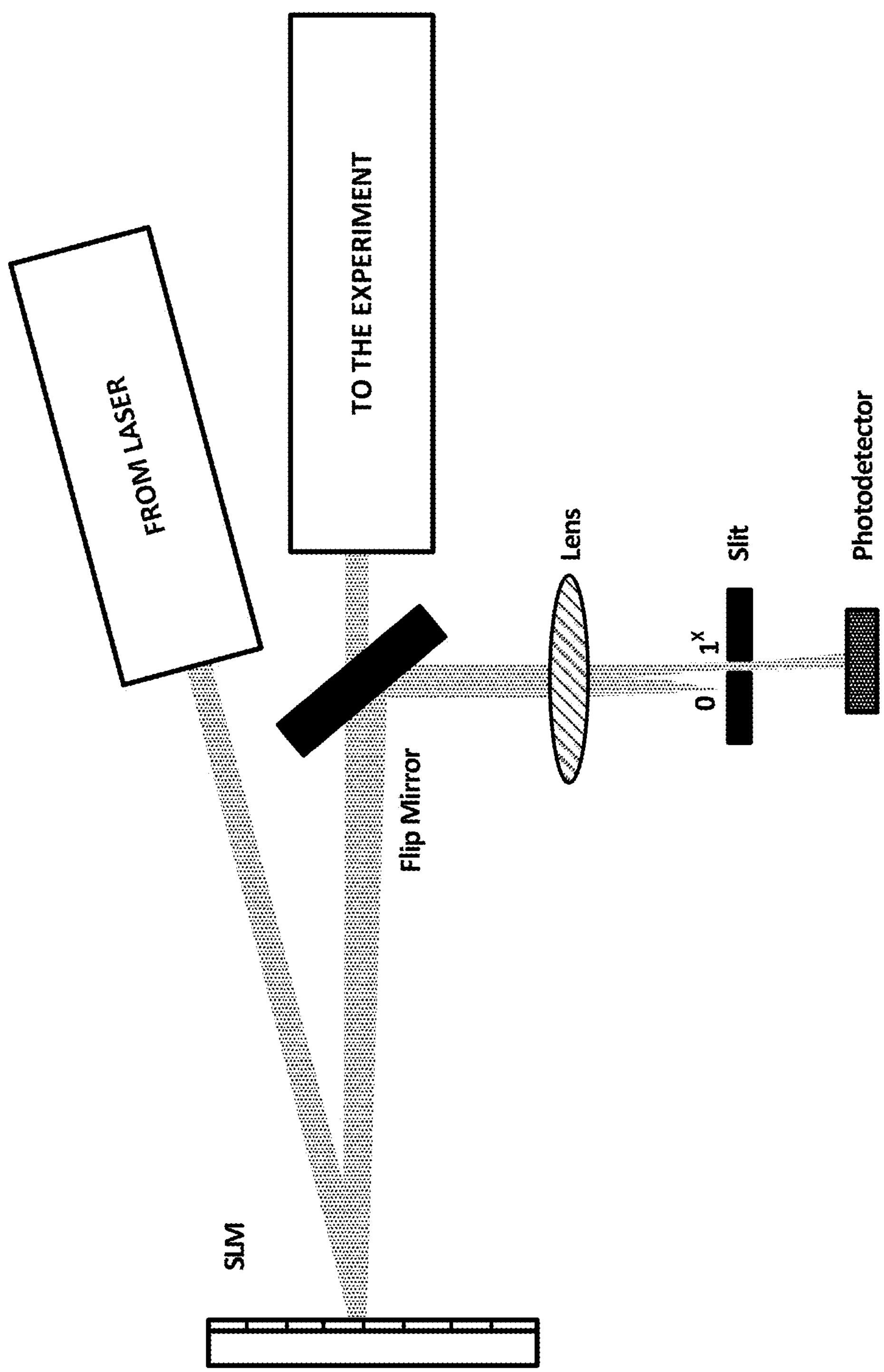
FIG. 7 is a block diagram of a SLM monitoring optical setup that may be used in accordance with some embodiments of the present technology.
Figure 8A:
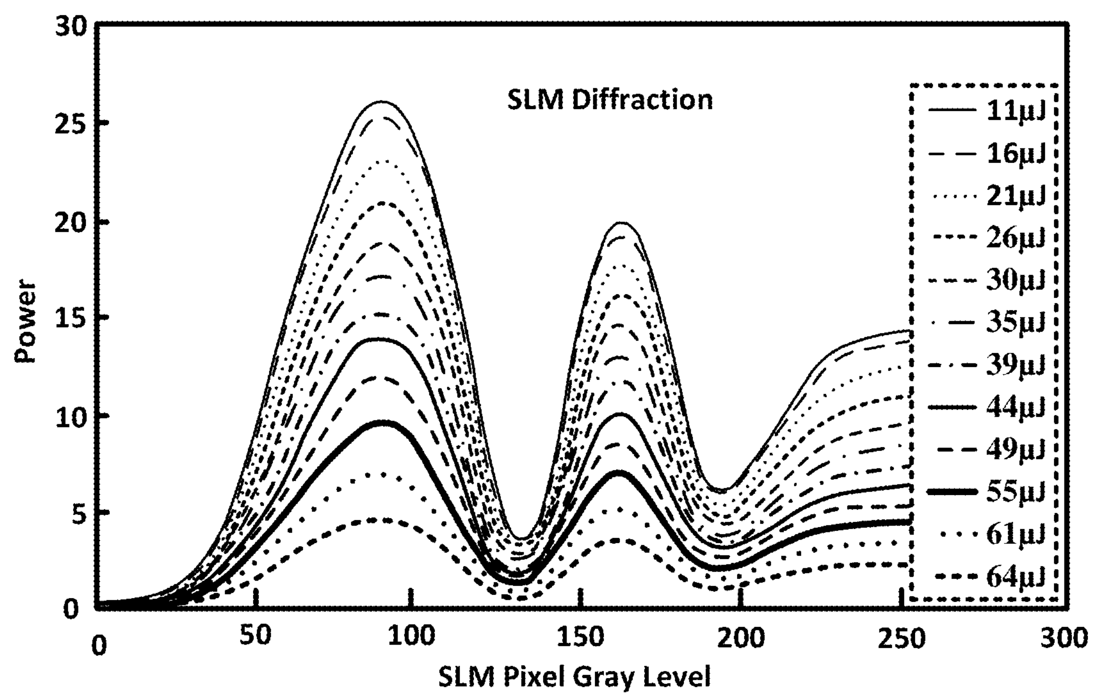
FIGS. 8A-8D illustrate results from SLM monitoring that may occur in one or more embodiments of the present technology.
Figure 8B:
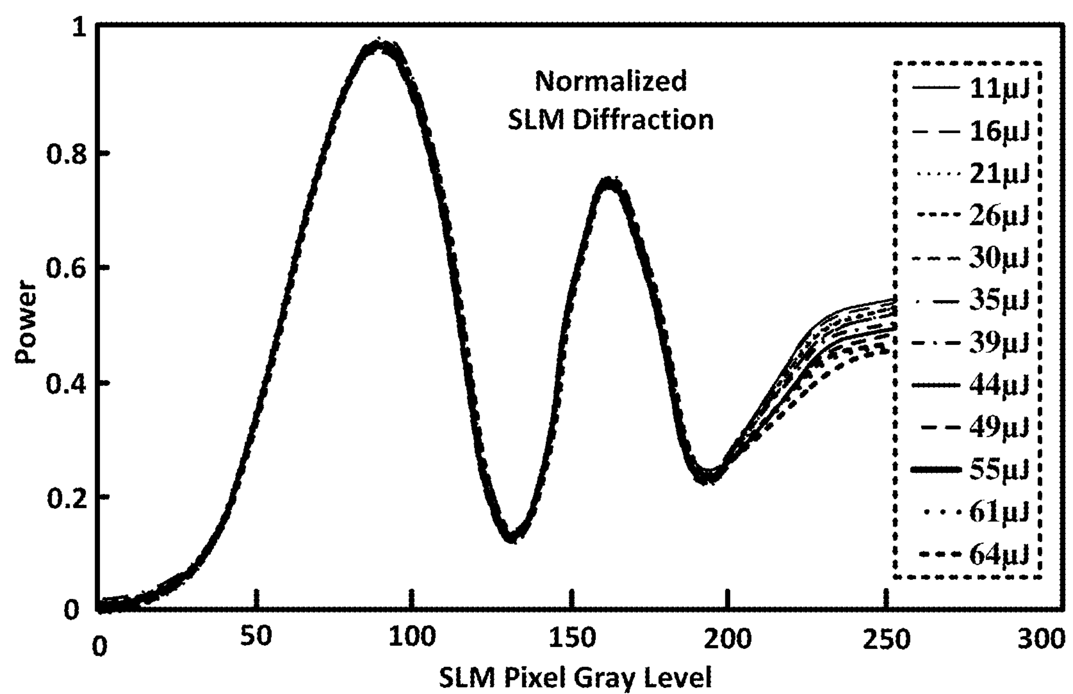
Figure 8C:
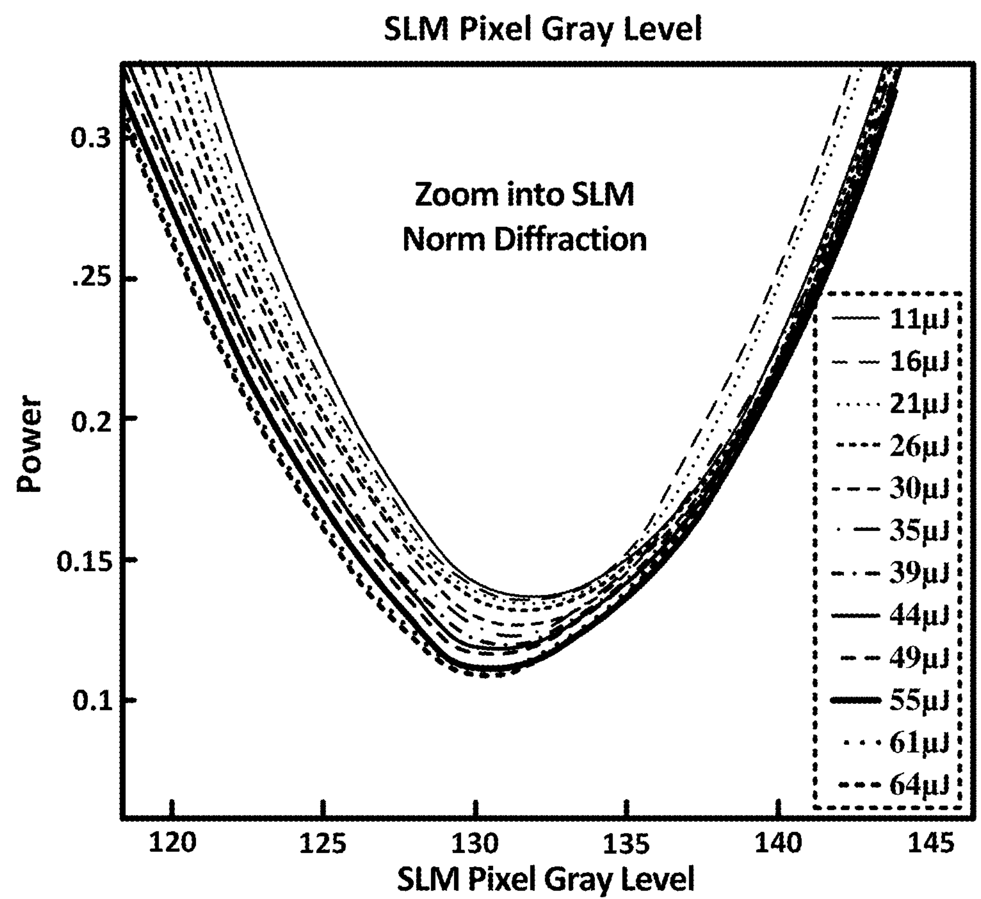
Figure 8D:
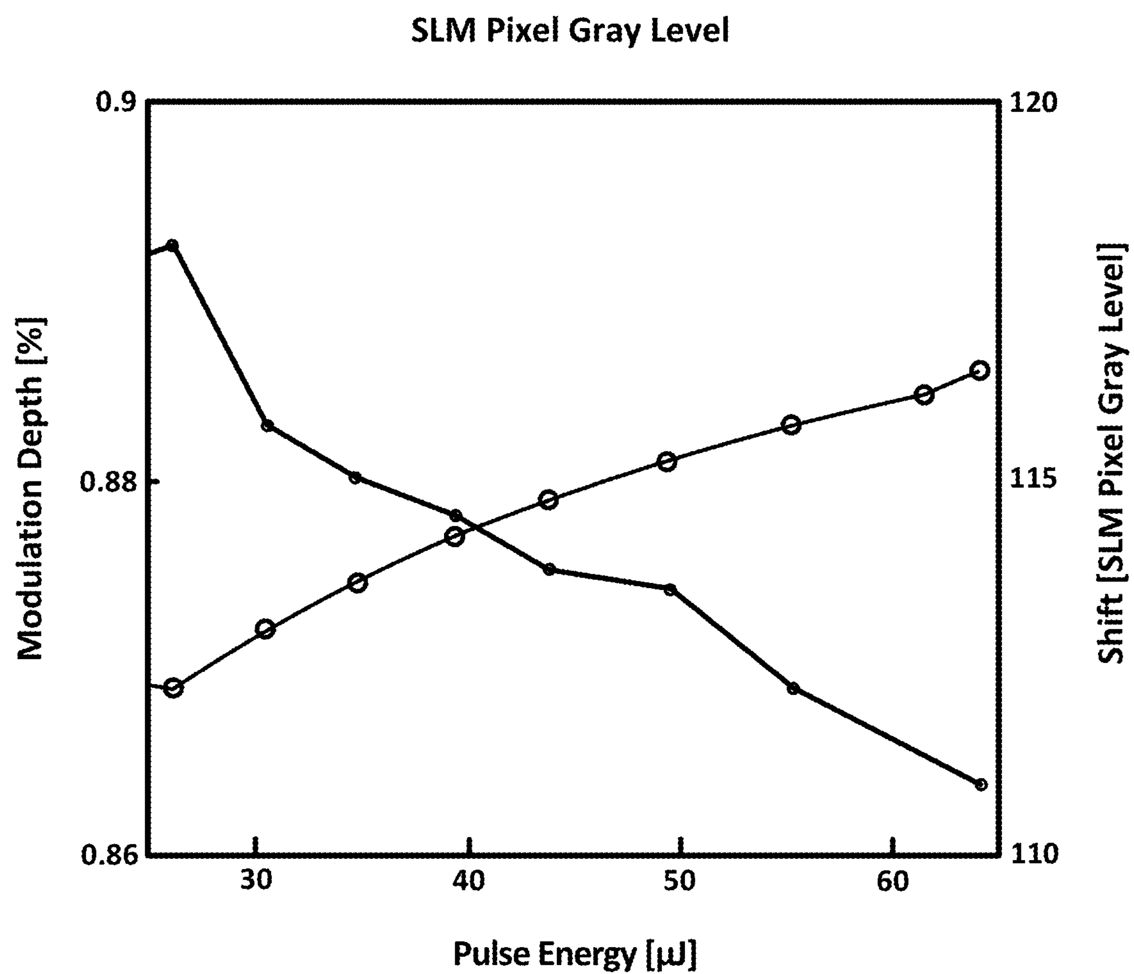

FIGS. 6A-6C depict several simulations of intermodal-phase-matching. Several modes in the GRIN fiber are shown and zoomed in on the experiment regime. The lines denote the Stokes (s), Pumps (p), and anti-Stokes (as) wavelengths, intersecting with the calculated modes, and indicating possible propagating waves in the GRIN fiber. The line between Stokes and Antistokes modes denotes allowed phase-matched combination, and crosses the pump spectral line. Energy conservation in FWM specify that this crossing point is the average between the momenta of the Stokes and anti-Stokes. Therefore, modal phase matching is achieved by a multimode pump whose average momenta equals the momentum at the crossing point. In addition to phase matching, the mode combination in FWM must conserve angular momentum between modes.

$$l_{as}+l_s-l_{P1}-l_{P2}=0,|$$

where $l_{wave}$ is the angular mode number. This term is satisfied in all the combination depicted in FIG. 7, where the pump is divided between the Stokes and anti-Stokes modes. In contrast, a single mode pump at $LP_{01}$ cannot produce a $LP_{21}$ anti-Stokes with $LP_{01}$ Stokes mode because angular momentum conservation prohibits this combination.

The FWM process in MMF can be described by the coupled amplitude equations of the nonlinear process (under quasi CW conditions). A single phase-matched configuration of the FWM anti-Stokes term can be defined as:

$$\frac{dA_{lm}^{as}}{dz} = \frac{in_2\omega_{as}}{c}\gamma^{as,p_1,p_2,s}A^{p1}A^{p2}A^{s*}e^{i\left[\beta_{l_s m_s}^{s}+\beta_{l_a m_a}^{as}-\beta_{l_1 m_1}^{p1}-\beta_{l_2 m_2}^{p2}\right]z},$$

where $\gamma^{as,p_1,p_2,s}$ represents the nonlinear coupling among spatial modes that depends on the spatial overlap integral of the participating modes.

$$\gamma^{as,p1,p2,s}=\iint F_{l_a m_a}{}^{as*}(x,y)F_{l_1 m_1}{}^{P1}(x,y)F_{l_2 m_2}{}^{P2}(x,y)F_{l_s m_s}{}^{s*}(x,y)dxdy,$$

where $F_{lm}{}^{wave}$ is the spatial mode profile at the specific mode of each wave.

SLM Damage Monitoring Procedure

Power handling measurements with pulsed lasers can be performed periodically in some embodiments and compared between measurements to ensure safe SLM operation. The SLM monitoring optical setup used in some embodiments is depicted in supplementary FIG. 7. In a test, a checkerboard pattern (2D grating) was written to the SLM and the 1st diffraction order intensity was collected as the difference in phase in the grating was varied from 0 to just over 1 wave (2π phase).

The obtained modulation curve helped verify that the SLM is still writing phase patterns and has more than a wave of modulation at the required incident power. It also enables comparative monitoring of long term performance and detection of degradation in the SLM capabilities. FIGS. 8A-8D show a typical series of characterization curves, with increasing laser power. A slight shift, less than five SLM-pixel-gray-level, in the phase response as a function of incident power is observed. This shift is a result of thermal effects and it is reversible at suitable power densities. Reduced modulation depth, less than 2%, with laser power can also be observed.

As long as the effects of increasing power are reversible and do not deteriorate over time, the SLM can be safely operated. A 512×512 liquid crystal spatial light modulator (e.g., Meadowlark Optics) can be used in some embodiments, and in various tests found it suitable for our experiment with SLM reflected maximal pulse energy of 65 μJ, at a repetition rate of 20 KHz, wavelength of 532 nm, and pulse duration 7 s.

Exemplary Computer System Overview

Aspects and implementations of the optical system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 9:
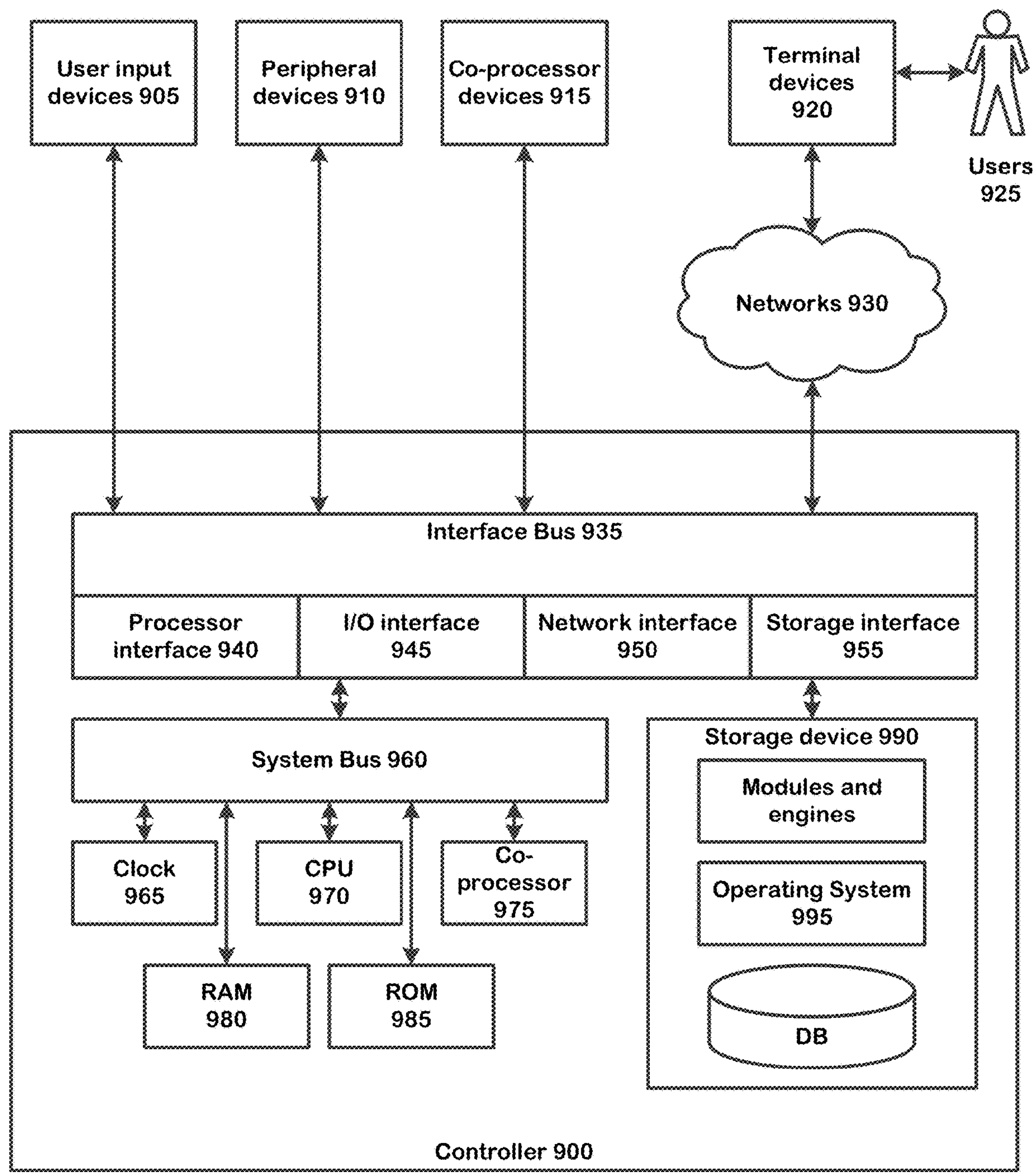
FIG. 9 is an example of a computer that maybe used in one or more embodiments of the present technology.

FIG. 9 is a block diagram illustrating an example machine representing the computer systemization of the controller. The controller 900 may be in communication with entities including one or more users 925 client/terminal devices 920, user input devices 905, peripheral devices 910, an optional co-processor device(s) (e.g., cryptographic processor devices) 915, and networks 930. Users may engage with the controller 900 via terminal devices 920 over networks 930.

Computers may employ central processing unit (CPU) or processor to process information. Processors may include programmable general-purpose or special-purpose microprocessors, programmable controllers, application-specific integrated circuits (ASICs), programmable logic devices (PLDs), embedded components, combination of such devices and the like. Processors execute program components in response to user and/or system-generated requests. One or more of these components may be implemented in software, hardware or both hardware and software. Processors pass instructions (e.g., operational and data instructions) to enable various operations.

The controller 900 may include clock 965, CPU 970, memory such as read only memory (ROM) 985 and random access memory (RAM) 980 and co-processor 975 among others. These controller components may be connected to a system bus 960, and through the system bus 960 to an interface bus 935. Further, user input devices 905, peripheral devices 910, co-processor devices 915, and the like, may be connected through the interface bus 935 to the system bus 960. The interface bus 935 may be connected to a number of interface adapters such as processor interface 940, input output interfaces (I/O) 945, network interfaces 950, storage interfaces 955, and the like.

Processor interface 940 may facilitate communication between co-processor devices 915 and co-processor 975. In one implementation, processor interface 940 may expedite encryption and decryption of requests or data. Input output interfaces (I/O) 945 facilitate communication between user input devices 905, peripheral devices 910, co-processor devices 915, and/or the like and components of the controller 900 using protocols such as those for handling audio, data, video interface, wireless transceivers, or the like (e.g., Bluetooth, IEEE 1394a-b, serial, universal serial bus (USB), Digital Visual Interface (DVI), 802.11a/b/g/n/x, cellular, etc.). Network interfaces 950 may be in communication with the network 930. Through the network 930, the controller 900 may be accessible to remote terminal devices 920. Network interfaces 950 may use various wired and wireless connection protocols such as, direct connect, Ethernet, wireless connection such as IEEE 802.11a-x, and the like.

Examples of network 930 include the Internet, Local Area Network (LAN), Metropolitan Area Network (MAN), a Wide Area Network (WAN), wireless network (e.g., using Wireless Application Protocol WAP), a secured custom connection, and the like. The network interfaces 950 can include a firewall which can, in some aspects, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including, for example, the access and operation rights of an object by an individual, a machine, and/or an application, and the circumstances under which the permission rights stand. Other network security functions performed or included in the functions of the firewall, can be, for example, but are not limited to, intrusion-prevention, intrusion detection, next-generation firewall, personal firewall, etc., without deviating from the novel art of this disclosure.

Storage interfaces 955 may be in communication with a number of storage devices such as, storage devices 990, removable disc devices, and the like. The storage interfaces 955 may use various connection protocols such as Serial Advanced Technology Attachment (SATA), IEEE 1394, Ethernet, Universal Serial Bus (USB), and the like.

User input devices 905 and peripheral devices 910 may be connected to I/O interface 945 and potentially other interfaces, buses and/or components. User input devices 905 may include card readers, finger print readers, joysticks, keyboards, microphones, mouse, remote controls, retina readers, touch screens, sensors, and/or the like. Peripheral devices 910 may include antenna, audio devices (e.g., microphone, speakers, etc.), cameras, external processors, communication devices, radio frequency identifiers (RFIDs), scanners, printers, storage devices, transceivers, and/or the like. Co-processor devices 915 may be connected to the controller 900 through interface bus 935, and may include microcontrollers, processors, interfaces or other devices.

Computer executable instructions and data may be stored in memory (e.g., registers, cache memory, random access memory, flash, etc.) which is accessible by processors. These stored instruction codes (e.g., programs) may engage the processor components, motherboard and/or other system components to perform desired operations. The controller 900 may employ various forms of memory including on-chip CPU memory (e.g., registers), RAM 980, ROM 985, and storage devices 990. Storage devices 990 may employ any number of tangible, non-transitory storage devices or systems such as fixed or removable magnetic disk drive, an optical drive, solid state memory devices and other processor-readable storage media. Computer-executable instructions stored in the memory may include one or more program modules such as routines, programs, objects, components, data structures, and so on that perform particular tasks or implement particular abstract data types. For example, the memory may contain operating system (OS) component 995, modules and other components, database tables, and the like. These modules/components may be stored and accessed from the storage devices, including from external storage devices accessible through an interface bus.

The database components can store programs executed by the processor to process the stored data. The database components may be implemented in the form of a database that is relational, scalable and secure. Examples of such database include DB2, MySQL, Oracle, Sybase, and the like. Alternatively, the database may be implemented using various standard data-structures, such as an array, hash, list, stack, structured text file (e.g., XML), table, and/or the like. Such data-structures may be stored in memory and/or in structured files.

The controller 900 may be implemented in distributed computing environments, where tasks or modules are performed by remote processing devices, which are linked through a communications network, such as a Local Area Network ("LAN"), Wide Area Network ("WAN"), the Internet, and the like. In a distributed computing environment, program modules or subroutines may be located in both local and remote memory storage devices. Distributed computing may be employed to load balance and/or aggregate resources for processing. Alternatively, aspects of the controller 900 may be distributed electronically over the Internet or over other networks (including wireless networks). Those skilled in the relevant art(s) will recognize that portions of the system may reside on a server computer, while corresponding portions reside on a client computer. Data structures and transmission of data particular to aspects of the controller 900 are also encompassed within the scope of the disclosure.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A system to control spatial, spectral, polarization and/or temporal distribution of light, the system comprising:
- a light source configured to generate a light;
- a spatial light modulator having a variable mask to modify one or more properties of the light generated by the light source;
- a medium having a proximal end to receive a modified light from the spatial light modulator and propagate the modified light to a distal end;
- a detection system to evaluate the one or more properties produced by the modified light; and
- a control system communicably coupled to the spatial light modulator and the detection system, configured to:
  - generate an updated mask that selectively tunes nonlinear interactions within the medium and enhances the one or more properties of the modified light within the medium or at the distal end of the medium; and
  - transmit a signal to the spatial light modulator to implement the updated mask.

2. The system of claim 1, wherein the light source is a pulsed laser such as a nanosecond pulsed laser, a picosecond pulsed laser, or a femtosecond pulsed laser.

3. The system of claim 1, wherein the detection system is at least one among a spectrometer, a detector array, a camera, a photodetector, an autocorrelator, or a pulse characterization system.

4. The system of claim 1, wherein the medium configured to transmit the light is a waveguide, a multicore fiber, a waveguide array, or a multimode fiber.

5. The system of claim 1, wherein the spatial light modulator is a liquid crystal spatial light modulator, a deformable mirror, a digital light projector, or a segmented mirror.

6. The system of claim 1, wherein the spatial light modulator includes independent macro pixels whose phase varies between zero and $2\pi$.

7. The system of claim 1, wherein the control system generates the updated mask using an optimization algorithm, genetic algorithm, or machine learning algorithm that optimizes an objective function.

8. The system of claim 1, wherein the control system controls at least one of the following properties: generation of nonlinear stimulated-Raman-scattering cascades and four-wave-mixing, a polarization of an output light, a pulse shape and duration of the output light, a spectrum of the output light, a spatial shape distribution of the output light, or reduction of nonlinear effects.

9. An optical system with dynamic feedback control to modify spatial, spectral, and/or temporal distributions of a light generated by a light source, the optical system comprising:
- a processor;
- a spatial light modulator having:
  - an input to receive the light generated by the light source;
  - a set of independent degrees of freedom that can be set by a variable mask to generate a modified light by changing one or more properties of the light generated by the light source;
- a medium to transmit the modified light entering a proximal end to a distal end, wherein the medium introduces one or more aberrations or nonlinearities into the modified light;
- a control system communicably coupled to the spatial light modulator to:
  - evaluate, using the processor, the one or more aberrations or nonlinearities in the modified light at the distal end of the medium;
  - generate a change to the variable mask that controls the one or more aberrations or nonlinearities at the distal end of the medium; and
  - provide feedback to the spatial light modulator to update the variable mask with the change identified by the control system.

10. The optical system of claim 9, wherein the light source is a nanosecond pulsed laser, a picosecond pulsed laser, or a femtosecond pulsed laser.

11. The optical system of claim 9, wherein the medium configured to transmit the light is a waveguide, a multi-core fiber, a waveguide array, or a multimode fiber and wherein the spatial light modulator is a liquid crystal spatial light modulator, a deformable mirror, a digital light projector, or a segmented mirror.

12. The optical system of claim 9, wherein the control system generates the change to the variable mask using an optimization algorithm, a genetic algorithm, or machine learning to optimizes an objective function.

13. A system comprising:
- means for generating a light;
- means for modifying one or more properties of the light;
- means for propagating a modified light to a destination;
- means for evaluating the one or more properties produced by the modified light at the destination or within the means for propagating the modified light;
- means for generating an updated mask that selectively tunes nonlinear interactions within the means for propagating the modified light and enhances the one or more properties of the modified light within or at the end of the means for propagating the modified light; and
- means for implementing the updated mask.

14. The system of claim 13, wherein the means for generating the light includes a pulsed laser such as a nanosecond pulsed laser, a picosecond pulsed laser, or a femtosecond pulsed laser.

15. The system of claim 13, wherein the means for evaluating the one or more properties produced by the modified light at the destination includes a spectrometer, a detector array, a camera, a photodetector, an autocorrelator, or a pulse characterization system.

16. The system of claim 13, wherein the means for propagating a modified light to the destination includes is a waveguide, a multicore fiber, a waveguide array, or a multimode fiber.

17. The system of claim 13, further comprising a liquid crystal spatial light modulator, a deformable mirror, a digital light projector, or a segmented mirror.

18. The system of claim 13, further comprising means for setting independent macro pixels whose phase varies between zero and 2π.

19. The system of claim 13, further comprising means for generating the updated mask using an optimization algorithm, genetic algorithm, or machine learning algorithm that optimizes an objective function.

20. The system of claim 13, further comprising means for controlling at least one of the following properties: generation of nonlinear stimulated-Raman-scattering cascades and four-wave-mixing, a polarization of an output light, a pulse shape and duration of the output light, a spectrum of the output light, a spatial shape distribution of the output light, or reduction of nonlinear effects.

* * * * *